(12) United States Patent
Mehta et al.

(10) Patent No.: US 6,303,325 B1
(45) Date of Patent: *Oct. 16, 2001

(54) METHOD FOR DETECTING ANALYTES

(75) Inventors: Harshvardhan B. Mehta, Fremont; Nurith Kurn, Palo Alto, both of CA (US)

(73) Assignee: Dade Behring Inc., Deerfield, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/087,839

(22) Filed: May 29, 1998

(51) Int. Cl.⁷ .................... G01N 33/538; G01N 33/542
(52) U.S. Cl. .................... 435/7.5; 435/7.1; 435/7.2; 435/7.32; 435/7.92; 435/7.93; 435/7.94; 435/7.95; 436/503; 436/506; 436/507; 436/509; 436/518; 436/533; 436/538; 436/534; 436/546; 436/540; 436/537; 436/528; 436/172; 436/819; 436/821; 436/827; 436/828
(58) Field of Search ..................... 436/503, 505, 436/507, 509, 518, 528, 533, 800, 838, 879, 827, 828, 537, 538, 540, 546, 524, 532, 534, 172; 435/7.93, 7.94, 7.95, 7.92, 7.32, 7.1, 7.2, 7.5

(56) References Cited

U.S. PATENT DOCUMENTS

| | | |
|---|---|---|
| 3,654,090 | 4/1972 | Schuurs et al. ............... 195/103.5 |
| 3,817,837 | 6/1974 | Rubenstein et al. ............ 195/103.5 |
| 3,996,345 | 12/1976 | Ullman et al. ................... 424/12 |
| 4,020,151 | 4/1977 | Bolz et al. ..................... 424/1.5 |
| 4,062,935 | 12/1977 | Masson et al. ................... 424/12 |
| 4,184,849 | 1/1980 | Cambiaso et al. ................ 23/230 |
| 4,228,237 | 10/1980 | Hevey et al. ...................... 435/7 |
| 4,271,140 | 6/1981 | Bunting ........................... 424/1 |
| 4,275,149 | 6/1981 | Litman et al. ..................... 435/7 |
| 4,318,980 | 3/1982 | Boguslaski et al. ................. 435/7 |
| 4,506,009 | 3/1985 | Lenhoff et al. .................... 435/7 |
| 4,659,678 * | 4/1987 | Forrest et al. .................. 436/512 |
| 4,778,751 | 10/1988 | El Shami et al. ................... 435/7 |
| 4,855,242 | 8/1989 | Soeldner ........................ 436/539 |
| 4,868,104 | 9/1989 | Kurn et al. ...................... 435/6 |
| 4,935,339 | 6/1990 | Zahradnik ........................ 435/5 |
| 4,959,303 | 9/1990 | Milburn et al. .................... 435/7 |
| 5,141,850 | 8/1992 | Cole et al. ..................... 436/525 |
| 5,185,243 | 2/1993 | Ullman et al. .................... 435/6 |
| 5,200,318 | 4/1993 | Rabin et al. .................. 435/7.21 |
| 5,212,063 | 5/1993 | Ofenlock-Hähnle et al. ....... 435/7.5 |
| 5,332,679 | 7/1994 | Simons et al. .................. 436/518 |
| 5,340,716 | 8/1994 | Ullman et al. .................... 435/6 |
| 5,378,608 | 1/1995 | Marui et al. ................... 435/7.5 |
| 5,407,802 | 4/1995 | Eisenbarth et al. ............ 435/7.21 |
| 5,475,086 | 12/1995 | Tobin et al. .................... 530/325 |
| 5,512,447 | 4/1996 | Baekkeskov et al. ............. 435/7.4 |
| 5,516,638 * | 5/1996 | Urnovitz et al. ............... 435/7.32 |
| 5,525,473 | 6/1996 | Hill et al. . | |
| 5,538,854 | 7/1996 | Faustman ..................... 435/7.24 |
| 5,547,847 * | 8/1996 | Hagopian et al. ................ 435/7.4 |
| 5,561,049 | 10/1996 | Vold et al. ..................... 435/7.1 |
| 5,589,574 | 12/1996 | Wolfert et al. ............... 530/388.26 |
| 5,614,368 | 3/1997 | Ghazarossian et al. ........... 435/7.5 |
| 5,627,080 | 5/1997 | Cheng et al. ................... 436/534 |
| 5,645,998 | 7/1997 | Atkinson et al. ................ 435/7.4 |
| 5,648,213 * | 7/1997 | Reddy et al. ..................... 435/6 |
| 5,674,692 | 10/1997 | Baekkeskov et al. ............ 435/7.21 |
| 5,674,978 | 10/1997 | Tobin et al. .................... 530/326 |
| 5,696,264 | 12/1997 | Albarella et al. ................. 544/257 |
| 5,705,626 | 1/1998 | Tobin et al. ................... 536/23.5 |
| 5,723,304 | 3/1998 | Abuknesha ..................... 435/7.9 |
| 5,723,343 | 3/1998 | Maclaren et al. ................ 436/506 |
| 5,723,344 | 3/1998 | Mabilat et al. .................. 436/518 |
| 5,731,147 | 3/1998 | Bard et al. ....................... 435/6 |
| 5,763,191 | 6/1998 | Knoll et al. .................... 435/7.1 |

FOREIGN PATENT DOCUMENTS

| | | |
|---|---|---|
| 0 322 813 A2 | 12/1988 | (DE) . |
| 0 070 527 A1 | 1/1983 | (EP) . |
| 0 168 689 A2 | 1/1986 | (EP) . |
| 0 410 893 A2 | 1/1991 | (EP) . |
| 0 515 194 A2 | 11/1992 | (EP) . |
| WO 9007117 A1 | 6/1990 | (WO) . |
| WO 9205446 A1 | 4/1992 | (WO) . |
| WO 9413804 A1 | 1/1994 | (WO) . |

OTHER PUBLICATIONS

Atkinson, et al., *Lancet* 335:1357–1360 (1990).

Cho, B.K., et al., *Bio Conjugate Chem.* (1997) 8(3), 338–346.

Cuatrecases, *J. Biol. Chem.* 245:3059 (1970).

Dafforn, A., et al., *Clinical Chemistry* vol. 36, pp. 1312–1316, 1990.

(List continued on next page.)

*Primary Examiner*—Long V. Le
*Assistant Examiner*—Gailene R. Gabel
(74) *Attorney, Agent, or Firm*—Patrick G Gattari; McDonnell Boehnen Hulbert & Berghoff; Cara Z Lowen

(57) ABSTRACT

The invention relates to methods of determining the presence or amount of an analyte in a sample suspected of containing the analyte, said method comprising the steps of: (a) bringing together in an aqueous medium to form a mixture: (i) the sample; (ii) at least one specific binder for the analyte; (iii) a first binding agent coupled to either (1) exogenous analyte or (2) the specific binder for the analyte; (iv) a support comprising a second binding agent; b) adding an activator to the mixture, wherein the activator binds the first binding agent and the second binding agent of the support to immobilize the first binding agent; c)determining the amount of the analyte in the sample by detecting the immobilized first binding agent, the presence or amount thereof being related to the presence or amount of the analyte in the sample.

32 Claims, No Drawings

OTHER PUBLICATIONS

Huang, W., et al., *Anal. Chem.* (1996) 68(9), 1646–1650.

Kurn, N., et al., *J. Bone & Mineral Research* vol. 9, Sup 1, p S402.

Libyh, M., et al. *Fr. Blood* (1997) 90(10), 3978–3983.

Linacre, P., et al., *Methodol. Surv. Biochem. Anal.* (1992) 22 (Bioanal. Approaches Drugs, Inc., Anti–Astamatics Metab.), 325–6.

Mehta, H.B., et al., *Clin. Chem.* 42, 263 (1996).

Milstein and Kohler, *Nature* 256:495–7 (1975).

Nakamura, et al., *Arch. Pathol. Lab. Med.* 112:869–877 (1988).

Ullman, E.F., et al. *PNAS* vol. 91, pp. 5426–5430, 1994.

Wallace, A., et al., *Pept. Res.* 7(1), 27–31 (1994).

Takeuchi, T, et al., "Enzymatic Solid–Phase Assay for Biotin and a Biotin–Benzodiazepine Conjugate" *Bioconjugate Chem.*, vol. 1, No. 4, (Jul./Aug. 1990), pp. 227–230.

Fayer, B. et al., "etermination of Humanized Anti–Tac In Human Serum By A Sandwich Enzyme Linked Immunosorbent Assay", *Journal of Immunological Methods*, vol. 186, (Mar. 8, 1995), pp. 47–54.

Hansen, S.I., et al., "Quantification of Bitin in Serum by Competition with Solid–Phase Biotin for Binding to Peroxidase–Avidin Conjugate", *Clinical Chemistry*, vol. 35, No. 8 (1989), pp. 1721–1722.

Bayer, E.A. et al., "A Sensitive Enzyme Assay for Biotin, Avidon and Streptavidin" *Analytical Biochemistry* 154, (1986), pp. 367–370.

Nyalala, J.O., et al., "Indirect Enzyme–Linked Method for Determining Biotin in Human Serum" *Journal of Immunoassay*, vol. 18 (1) (1997), pp. 1–19.

Dooley, Steven, et al., "A Simple and Sensitive Enzyme–Mediated Assay of Biotin", *BioTechniques*, vol. 13, No. 4, (1992), pp. 543 546.

Mehta, H. B., et al., "DELISA: Sensitive Nonisotopic Assay for $GAD_{65}$ Autoantibodies, a Key Risk–assessment Marker for Insulin–dependent Diabetes Mellitus" *Clinical Chemistry* 42:2, (1996), pp. 263–269.

Remy, I. et al., "Potentiality of an Organometallic Labeled Streptavidin–Biotin System in Metalloiommunoassay" *Fr. J. Pharm. Biomed. Anal.* (1991) 9 (10–12), 965–7 (abstract) only.

Tanaka, S., et al., "Non–isotopic receptor asay for benzodiazepines using a biotin–labed igand and biotin–immobilized microtiter plate", J. Chromatogr (1992), 597 (1–2), 443–8 (abstract) only.

English Language Abstract of DE 3629194.
English Language Abstract of CA 2004094.
English Language Abstract of DE 3829245.
English Language Abstract of JP 4249770.
Abstract of WO 9732984.
Abstract of US 5645998.
Abstract of US 5512447.
Abstract of WO 9609552.
Abstract of WO 9507464.
Abstract of 9007117.
English language Abstract of RO 95315.
English language Abstract of DE 2902400 A.
English language Abstract of EP 201079.
Abstract of WO 8804777.
Abstract of WO 9403530.
Abstract of WO 9402515.
English language Abstract of EP 574000.
English language Abstract of JP 04066871 A2–920303.
English language Abstract of JP 04066870 A2–920303.
Abstract of US 5296347.
English language Abstract of EP 93 572217.

\* cited by examiner

METHOD FOR DETECTING ANALYTES

FIELD OF THE INVENTION

This invention relates to the detection of analytes in a sample using an immunoassay. More particularly the invention relates to the detection of analytes in a sample using a method that eliminates a transfer step.

BACKGROUND OF THE INVENTION

Processes that enable the detection or quantification of substances present at very low concentrations in a sample are important tools in many analytical areas. Such processes include methods of measuring low concentrations of analytes in a clinical sample of biological fluids such as urine and blood and of detecting small amounts of drugs and trace residues of chemicals such as pesticides and herbicides in a sample.

In order to be useful, methods of determining low levels of substances in fluid samples must be highly sensitive and accurate. Receptor based assays such as immunoassays exemplify such methods and are currently used to detect substances in very low concentrations in clinical samples of biological fluids such as blood and urine. Immunoassays detect these substances by using an antibody that reacts specifically with the substance to be tested (e.g., a primary antibody).

The detection of antibodies is a useful tool in the diagnosis of diseases caused by antigens. Similarly, detection of autoantibodies is useful in determining a patient's risk of developing a disease. For example, there has been much research relating to detecting autoantibodies as a risk factor for patients developing insulin dependent diabetes mellitus ("IDDM"). There are numerous autoantibodies that are believed to be indicative of IDDM, which is also known as Type I Diabetes or juvenile diabetes. These include insulin autoantibodies, pancreatic islet cell antigen autoantibodies, and most recently autoantibodies to the 65 kd isoform of glutamic acid decarboxylase ("GAD65").

Autoantibodies to GAD65 have been suggested to be one of the earliest markers for the development of IDDM. These autoantibodies are present several years before clinical onset of IDDM, at which time intervention steps could be taken to deter the progression of the disease.

Specific antibodies can only be measured by detecting binding to their antigen or a mimic thereof. Although certain classes of immunoglobulins containing the antibodies of interest may in some cases be separated from the sample prior to the assay (Decker, et al., EP 0,168,689 A2), in all assays, at least some portion of the sample immunoglobulins are contacted with antigen. For example, in assays for specific IgM, a portion of the total IgM can be adsorbed to a surface and the sample removed prior to detection of the specific IgM by contacting with antigen. Binding is then measured by detection of the bound antibody, detection of the bound antigen or detection of the free antigen.

For detection of bound antibody, a labeled anti-human immunoglobulin or labeled antigen is normally allowed to bind antibodies that have been specifically adsorbed from the sample onto a surface coated with the antigen, Bolz, et al., U.S. Pat. No. 4,020,151. Excess reagent is washed away and the label that remains bound to the surface is detected. This is the procedure in the most frequently used assays, or example, for hepatitis and human immunodeficiency virus and for numerous immunohistochemical tests, Nakamura, et al., *Arch. Pathol. Lab. Med.* 112:869–877 (1988). Although this method is relatively sensitive, it is subject to interference from non-specific binding to the surface by non-specific immunoglobulins that can not be differentiated from the specific immunoglobulins.

Another method of detecting bound antibodies involves combining the sample and a competing labeled antibody, with a support-bound antigen, Schuurs, et al., U.S. Pat. No. 3,654,090. This method has its limitations because antibodies in sera will bind numerous epitopes, making competition inefficient.

For detection of bound antigen, the antigen can be used in excess of the maximum amount of antibody that is present in the sample or in an amount that is less than the amount of antibody. For example, radioimmunoprecipitation ("RIP") assays for GAD autoantibodies have been developed and are currently in use, Atkinson, et al., Lancet 335:1357–1360 (1990). However, attempts to convert this assay to an enzyme linked immunosorbent assay ("ELISA") format have not been successful. The RIP assay is based on precipitation of immunoglobulins in human sera, and led to the development of a radioimmunoassay ("RIA") for GAD autoantibodies. In both the RIP and the RIA, the antigen is added in excess and the bound antigen:antibody complex is precipitated with protein A-Sepharose. The complex is then washed or further separated by electrophoresis and the antigen in the complex is detected. Other methods of detecting bound antigen are described in Masson, et al., U.S. Pat. No. 4,062,935; Soeldner, et al., U.S. Pat. No. 4,855,242; Ito, et al., EP 0,410,893 A2; Cambiaso, et al., U.S. Pat. No. 4,184,849 and Uchida, et al., EP 0,070,527 A1.

There has been much research in the area of evaluating useful markers for determining the risk factor for patients developing diseases, such as IDDM. For example, markers used to detect IDDM include insulin autoantibodies, Soeldner, et al., supra and circulating autoantibodies to glutamic acid decarboxylase ("GAD"), Atkinson, et al., PCT/US89/05570 and Tobin, et al., PCT/US91/06872. In addition, Rabin, et al., U.S. Pat. No. 5,200,318 describes numerous assay formats for the detection of GAD and pancreatic islet cell antigen autoantibodies. GAD autoantibodies are of particular diagnostic importance because they occur in preclinical stages of the disease, which may make therapeutic intervention possible. However, the use of GAD autoantibodies as a diagnostic marker has been impeded by the lack of a convenient, nonisotopic assay.

One assay method involves incubating a support-bound antigen with the sample, then adding a labeled anti-human immunoglobulin. This is the basis for numerous commercially available assay kits for antibodies such as the Syn$^{elisa}$ kit which assays for autoantibodies to GAD65, and is described in product literature entitled "Syn$^{elisa}$ GAD II-Antibodies" (Elias USA, Inc.). Substantial dilution of the sample is required because the method is subject to high background signals from adsorption of non-specific human immunoglobulins to the support.

Many of the assays described above involve detection of antibody that becomes bound to an immobilized antigen. This can have an adverse affect on the sensitivity of the assay due to difficulty in distinguishing between specific immunoglobulins and other immunoglobulins in the sample, which bind non-specifically to the immobilized antigen. There is not only a need to develop an assay that avoids non-specific detection of immunoglobulins, but there is also the need for an improved method of detecting antibodies that combines the sensitivity advantage of immunoprecipitation assays with a simplified protocol. Finally, assays that can help evaluate the risk of developing diseases such as IDDM are medically and economically very important. The present invention addresses these needs.

In immunoassays the sequence of binding reactions is usually determined by the sequence of addition of assay specific reagents. Preferred assay protocols minimize the number of assay steps, such as reagent addition, wash steps, and transfers of the assay mixture from one container to another. Early addition of reagents designed to react at late stages of the assay procedure may slow down or prevent required binding interactions. In particular, it is desirable to avoid premature binding to surfaces because reactions at surfaces often suffer from adverse binding kinetics. It would be useful to have a means to carry out the binding steps in an assay mixture that is in contact with a specifically activated surface without premature binding of the resulting immune complex to the surface. It would be useful to eliminate the need to transfer the assay mixture from an inert container in which binding occurs to a surface-activated container where binding of the complex to the surface facilitates its separation.

We have developed a process that simplifies the detection of auto-antibodies such as GAD. U.S. Pat. No. 5,561,049 describes a depletion ELISA procedure (DELISA) for the detection of auto-antibodies. In that invention, the sample is combined with an antigen that binds the antibodies in the sample to form an antigen:antibody complex. In an example of this method, Protein A is used to bind the complex and not bind the antigen when the antigen is not part of the complex. Streptavidin is used to selectively bind the antigen relative to binding the complex when the complex is bound to the Protein A. Protein A can be bound to a soluble polymer or suspendable solid phase. The streptavidin can be bound to a solid phase. Instead of streptavidin, a molecule consisting of two receptors that bind the antigen can be used where each receptor is bound to a signal producing system member. For example, a biotin-GAD conjugate, when combined with a serum sample, binds to any GAD auto-antibody present in the sample. A protein A-dextran conjugate is then added which binds all the immunoglobulins in the sample including the GAD auto-antibody. Upon transfer of this solution to a streptavidin-coated well, only free biotin-GAD conjugate that is not bound to the auto-antibody can bind to the surface. After removing the solution from the well, the free conjugate is detected by measuring the amount of an enzyme labeled anti-GAD antibody that can bind to the surface. In this method the assay mixture must be kept separate from the streptavidin coated surface until the binding reactions are complete in order to avoid detecting conjugate that would otherwise have bound to auto-antibody. It would be useful to have an assay that eliminates the need to transfer the assay mixture to the streptavidin coated surface.

In addition to the use of immunoassays in a clinical setting, immunoassays are useful in other applications. For example, in view of the widespread use of chemicals in the environment, in the form of pesticides and herbicides, there is a need for a simple, quantitative, and accurate method of measuring the levels of these chemicals which may be present in low concentrations in soil, food products, and water samples.

It is therefore desirable to have a method of determining analyte concentrations in fluid samples which is simple and rapid. Such an assay should be useful for any sample that can be homogenized into a fluid medium. It is especially desirable to be able to determine analytes in biological and other samples. It is further desirable to have a method which does not use toxins or expensive reagents. It also highly desirable to have a method that does not require a separation or collection step.

It would be useful to have an immunoassay procedure that is easier and faster to use. It would be useful to have an assay that minimizes the number of transfer steps and permits the binding reactions including binding to the surface to be carried out in the same well.

SUMMARY OF THE INVENTION

Biotin and other small molecule labels are often attached to a ligand or receptor reagent in binding assays to facilitate separation without adversely affecting binding kinetics. The present method permits specific binding reactions to take place in homogeneous solution where diffusion is fast. After the reaction takes place, the mixture contacted with a surface that is coated with a capture receptor for the label. After binding of the immune complex to the surface it is separated from the other assay components and detected.

The present invention relates to a method of determining the presence or amount of an analyte in a sample suspected of containing the analyte, said method comprising the steps of:

(a) bringing together in an aqueous medium to form a mixture:
  (i) the sample;
  (ii) at least one specific binder for the analyte;
  (iii) a first binding agent coupled to either (1) exogenous analyte or (2) the specific binder for the analyte;
  (iv) a support comprising a second binding agent;

b) adding an activator to the mixture, wherein the activator binds the first binding agent and the second binding agent of the support to immobilize the first binding agent;

c) determining the amount of the analyte in the sample by detecting the immobilized first binding agent, the presence or amount thereof being related to the presence or amount of the analyte in the sample.

In certain embodiments of the methods, the first binding agent and the second binding agent are the same. In these embodiments the activator can be a multivalent molecule. In preferred embodiments where the first and second binding agents comprise biotin, the activator comprises avidin, streptavidin or anti-biotin antibody. Preferably, the number of binding sites on the activator, e.g., avidin or streptavidin, added is less than or equal to the total equivalents of the first and second binding agent, e.g., biotin, bound to the support and the antigen. More preferably, the number of binding sites on the activator is one-half the total equivalents of biotin comprising the first and second binding agents.

If the first binding agent and the second binding agent are different, the activator is a heterofunctional molecule having a first binding site that binds the first binding agent and a second binding site that binds the second binding agent.

In certain embodiments, the first binding agent is a receptor and the activator comprises a multi-valent ligand therefor. In an example of such an assay, the first binding agent comprises folate binding protein and the activator comprises a folate-dextran conjugate.

The determining step of the method comprises providing one or more signal producing system members, and measuring the signal produced by said signal producing system members, the presence or amount thereof being related to the presence or amount of said analyte in said sample. Preferably at least one of said signal producing system members is selected from the group consisting of fluorescers, enzymes, chemiluminescers, photosensitizers and suspendable particles.

Preferably the support comprises the surface of a container, beads, glass, polystyrene, polypropylene, polyethylene, dextran, nylon, amylases, natural and modified celluloses, polyacrylamides, agaroses and magnetic particles, e.g., magnetite.

The invention also relates to a modified DELISA assay format in which the analyte comprises an antibody, the molecule that binds the analyte is an antigen to the antibody, the first binding agent is coupled to exogenous antigen. In such an assay, in the reaction mixture, the antibody binds the exogenous antigen to form a first binding agent/antigen/antibody complex. Between steps (a) and (b) above, a masking compound that binds the complex and does not bind the antigen when the antigen is not part of the complex is added. In these assays, the activator selectively binds the unmasked first binding agent coupled to the antigen relative to binding the masked complex and also binds the second binding agent. To measure the amount or presence of the antigen, a label bound to a second specific binder to the antigen in the complex is added. The amount of label is detected.

Examples of masking compound include, but are not limited to antibodies to immunoglobulins, complement factor C1q, rheumatoid factor, protein G and protein A. Preferably the the masking compound is bound to a suspendable solid phase or soluble polymer. An example of a suspendable solid phase is a particle comprised of a material selected from the group consisting of polymers, ceramic and glass. When the masking compound is bound to a soluble polymer, preferred polymers have a molecular weight of over 250,000. A particularly preferred polymer comprises dextran.

The determining step of this assay involves the detection of enzyme activity, luminescence or light absorbance. In some embodiments the antigen is bound to a member of a signal producing system. In other embodiments a second specific binder is added that binds said antigen, wherein said receptor is directly or indirectly bound to a label. In certain embodiments the support is separated from the mixture and contacted with a second specific binder for said antigen.

The modified DELISA assay method of the present invention is especially useful for detecting an autoantibody to glutamic acid decarboxylase or insulin.

In certain embodiments, the determining step comprises contacting said immobilized antigen with one or more signal producing system members, and measuring the signal produced by said signal producing system members, the presence or amount thereof being related to the presence or amount of said antibodies in said sample. Preferably, at least one of said signal producing system members is selected from the group consisting of fluorescers, enzymes, chemiluminescers, photosensitizers and suspendable particles.

The invention further relates to competitive assays wherein either the specific binder or the exogenous analyte is detectable and the first binding agent is coupled to exogenous analyte and wherein the determining step comprises detecting the detectable specific binder or exogenous analyte. In some competitive assays, the analyte in the sample competes with the analyte that is coupled to the first binding agent for binding with the specific binder, and the analyte coupled to the first binding agent forms a complex with the specific binder in an amount that is proportional to the amount of analyte in the sample. In these assays, the activator binds the first binding agent in the complex and the second binding agent. In such assays, the detectable analyte comprises a member of a signal producing system, and the determining step comprises measuring the signal produced by said the signal producing system, the presence or amount thereof being related to the presence or amount of said analyte in said sample. Preferably at least one of said signal producing system members is selected from the group consisting of fluorescers, enzymes, chemiluminescers, photosensitizers and suspendable particles.

The invention still further relates to sandwich assays in which the mixture of step (a) comprises two specific binders for the analyte, a first and second specific binder, wherein the first specific binder is coupled to the first binding agent and the second specific binder is detectable. The presence of or amount of label is directly proportional to the amount of analyte present in the sample. In certain of these assays, the detectable specific binder comprises a member of a signal producing system, and the determining step comprises measuring the signal produced by said the signal producing system, the presence or amount thereof being related to the presence or amount of said analyte in said sample. Preferably at least one of said signal producing system members is selected from the group consisting of fluorescers, enzymes, chemiluminescers, photosensitizers and suspendable particles.

The invention further relates to kits for detecting the presence of or determining the amount of analyte in a fluid sample comprising: (1) at least one specific binder for the analyte; (2) a first binding agent coupled to either (a) exogenous analyte or (b) the specific binder for the analyte; (3) a support comprising a second binding agent; and (4) an activator t hat binds the first binding agent and the second binding agent of the support to immobilize the first binding agent.

In a preferred kit for performing a DELISA assay, the analyte comprises an antibody, the specific binder is an antigen to the antibody, the first binding agent is biotin which is coupled to antigen, the second binding agent comprises biotin which is bound to the walls of a container, and the activator comprises streptavidin.

In preferred kits for performing a modified DELISA assay, the kit further comprises a masking compound bound to a suspendable solid phase or soluble polymer. The suspendable solid phase is preferably a particle comprised of a material selected from the group consisting of polymers, ceramic and glass. Preferred masking compounds include antibodies to immunoglobulins, complement factor C1q, rheumatoid factor, protein G and protein A, which can be selected depending on the analyte to be tested.

Certain kits of the present invention further comprise at least one member of a signal producing system. At least one of said signal producing system members is selected from the group consisting of fluorescers, enzymes, chemiluminescers, photosensitizers and suspendable particles.

The methods of the present invention are particularly applicable to systems in which the mixture is moved by capillary forces from an inert site to a site that has a second binding agent. It is also useful for methods in which the solid surface can be added to the mixture such as when latex particles are used, as distinct from having to transfer the mixture to a second container that has a capture receptor on its surface. It is also useful when the surface of the container of the assay mixture has the second binding agent because the assay mixture must be transferred from an uncoated container to a coated container.

The methods of the present invention represent an improvement over capture methods exemplified by, e.g., U.S. Pat. Nos. 4,271,140 and 4,935,339 in that the binding reaction is carried out in the presence of the activated surface, and an activator such as streptavidin is added to initiate binding to the surface following binding of the analyte to its specific binding partner. In one embodiment, the method is an improvement over the DELISA method of U.S. Pat. No. 5,561,049 for the detection of auto-antibodies.

An added benefit of reduced assay complexity, as is accomplished by the present invention, is the increased accuracy due to reduction of steps, each contributing to assay variability.

DESCRIPTION OF INVENTION

The process of the present invention will be illustrated in connection with the detection of auto-antibodies to the pancreatic auto-antigen, glutamic acid decarboxylase (GAD) and a specific ELISA format. However, the invention is broadly applicable to a wide variety of analytes and assay formats, e.g., competitive and sandwich assays, and is not limited to, antibodies or to the ELISA format.

We have previously reported a novel ELISA format, DELISA, for measuring GAD autoantibodies in serum (U.S. Pat. No. 5,561,049 and Mehta, H. B., et al., *Clin. Chem.*, 42, 263 (1996)). Briefly, DELISA protocol involves reaction between serum and bGAD in a polypropylene microtiter plate. Sufficient soluble PrA-dextran conjugate is then added to bind the immunoglobulins in the sample, including GAD autoantibodies to which GAD is bound. The mixture is transferred from a polypropylene plate to a streptavidin coated microtiter plate, which binds free bGAD. Unbound components of the reaction mixture are then washed off and streptavidin bound bGAD is specifically detected by reacting peroxidase-GAD MAb conjugate. Excess conjugate is then removed by washing and color is developed by reaction with peroxidase substrates. The color development is stopped by sulfuric acid addition and the absorbance is read at 450 nm. This method overcomes the problem of poor sensitivity and specificity associated with conventional ELISAs, and performs comparably with RBAs (Mehta, H. B., et al., *Clin. Chem.*, 42, 263 (1996)). However, the method requires two plates, a plate-to-plate transfer step of reaction mixture, washing of streptavidin coated plate just prior to use in the assay, and a total assay time of about 5.5 h.

Before proceeding further with the description of the specific embodiments of the present invention, a number of terms will be defined.

Analyte: The molecule in the sample that is detected by the assays of the present invention, including small molecules, antibodies, antigens, ligands and anti-ligands. The method of this invention is useful for measuring any analyte of interest. The method of this invention is especially useful for measuring small ligands or haptens. The following is a partial list of substances in whole serum to which this assay would be applicable: acetaminophen, N-acetylprocainamide, amikacin, amitriptyline, amobarbital, butabarbital, caffeine, carbamazepine, cocaine, codeine, cortisol, diazepam, digitoxin, digoxin, ethosuximide, gentamicin, glutethimide, hexobarbital, ibuprofen, kanamycin, lidocaine, methsuximide, morphine, netilmicin, nortriptyline, oxycodone, pentobarbital, phencyclidine phenobarbital, phenytoin, primidone, procainamide, propoxyphene, quinidine, salicylic acid, secobarbital, theophylline, thyroxine, tobramycin, valproic acid and vancomycin. The assays of the present invention are useful for detecting cancer antigens, such as, cathepsin D, epidermal growth factor receptor (EGFr), c-erbB-2 protein, cytokeratin, alphafetoprotein (AFP), carcinoembryonic antigen (CEA), urinary gonadotropin peptide (UGP), and other cancer marker proteins, and viral antigens, especially those associated with cancer such as human papilloma virus (HPV) antigens, hormones, such as thyroid stimulating hormone (TSH), and steroid and thyroid hormones; viruses, allergens, bacteria and toxins. This assay is also useful for detecting the presence of larger proteins, such as human chorionic gonadotrophin (HCG), ferritin, C-reactive protein (CRP), apolipoproteins, hepatitis antigen and immunoglobulins. Examples of antibodies include complete immunoglobulins or fragments thereof, and include the various classes and isotypes, such as IgA, IgD, IgE, IgG1, IgG2a, IgG2b and IgG3 and IgM.

The assays of the present invention are also useful for detecting and measuring low amounts of substances in samples other than biological fluids. For example, this assay is useful in detecting and determining low levels of contaminants in environmental samples of soil, water and food products. The following is a partial list of examples of herbicides, pesticides and other contaminants for which this assay would be useful: Atrazine, Chlordane, Chlorneb (and other chlorinated pesticides), DDT, Demeton, Diazinon (and other organophosphorous pesticides), Diethylphthalate (and other phthalate esters), Dimethoate, Dimethylphthalate, Dimethoate, Etridiazole, Hexachlorobenzene, Malathione, Methyl parathion, Molinate, Naphthalone, Phorate, Propachlor, Simazine, Triflurilin and 2,4-D (and other Phenoxyacid herbicides).

The above lists are meant to be exemplary and are not intended to limit the scope of the present invention.

Antigen: A compound against which antibodies can be raised, and which is capable of binding to an antibody to form specific antibody:antigen complexes. The antigen is bound by the antibody analyte, usually a biomolecule, mammalian, viral or microbiological in origin or a mimic thereof, or other molecules of synthetic or natural origin that are in the environment such as drugs, pesticides, environmental contaminants and the like. The antigen may be used in the assay in its natural form or it may be modified provided the modification does not interfere with its antigenicity. Typical modifications include binding covalently or non-covalently to the antigen, a specific binding pair member and/or a detectable label, either or both of which can facilitate detection of the antigen.

Antibodies useful in the methods of the present invention can be monoclonal or polyclonal and can be prepared by techniques that are well known in the art such as immunization of a host and collection of sera from which the immunoglobulin can be separated by known techniques (polyclonal), by preparing continuous hybrid cell lines and collecting the secreted protein (monoclonal) as described by Milsrein and Kohler, *Nature* 256:495–7 (1975), or by cloning and expressing nucleotide sequences or mutagenized versions thereof coding at least for the amino acid sequences required for specific binding of natural antibodies. Antibodies may include the complete immunoglobulin or a fragment thereof, and include the various classes and isotypes, such as IgA, IgD, IgE, IgG1, IgG2a, IgG2b and IgG3 and IgM. Fragments may include Fab, Fv, F(ab')2 and Fab.

Sample suspected of containing the analyte: any sample which is reasonably suspected of containing the analyte of interest, can be analyzed by the methods of the present invention. The sample is typically an aqueous solution such as a body fluid from a host, for example, urine, whole blood, plasma, serum, saliva, semen, stool, sputum, cerebral spinal fluid, tears, mucus, or the like, but preferably is plasma or serum. Or as described above, the sample can be samples of water, soil or food products. The sample can be pretreated as described below and can be prepared in any convenient medium which does not interfere with the assay. An aqueous medium is preferred.

Member of a specific binding pair ("sbp" member): one of two different molecules having an area on the surface or in a cavity that specifically binds to and is therefore defined as complementary with a particular spatial and polar organization of the other molecule. The sbp members can be referred to as ligand and receptor such as members of an immunological pair, e.g., antigen-antibody. As used herein, the term "ligand" refers to any organic compound for which a receptor naturally exists or can be prepared and the term "receptor" refers to any compound or composition capable of recognizing a particular spatial and polar organization of a molecule, i.e., epitopic or determinant site. Complementary sbp members bind to one another, as for example, a ligand and its complementary receptor. Sbp members can be immunological pairs such as antigen and antibody, or non-immunological pairs such as avidin and biotin or the complementary strands o f an oligonucleotide. Sbp members can also be small molecules or residues of small molecules and their receptors. Small molecules have a molecular weight of from 100–2000, preferably 150–1000, and a receptor for the small molecule either exists or can be prepared. Examples of small molecules include derivatives of biotin, lysergic acid, fluorescein or a fluorescein derivative, and vitamin B12, with the corresponding receptors being avidin or streptavidin, anti-lysergic acid, anti-fluorescein and intrinsic factor, respectively. Small molecules are often covalently bound to other sbp members to form a conjugate having at least one, and frequently 2–20, small molecules. Bonding of the small molecule to the sbp member may be accomplished by chemical reactions which result in replacing a hydrogen atom of the small molecule with a bond to the sbp member or by a linking group between the small molecule and the sbp member of any size but preferably no larger than necessary to permit binding to the conjugate of both a receptor for the small molecule and the sbp member. Antibodies to small molecules can be prepared by immunizing animals with an immunogen prepared by linking the small molecule to an immunogenic carrier.

Specific binder: means a molecule or compound that specifically binds the analyte of interest and includes antibodies, antigens, ligands, receptors or fragments or analogs thereof.

Support or surface: The solid phase is typically a support or surface, which is a porous or non-porous water insoluble material that can have any one of a number of shapes, such as strip, rod, particle, including beads and the like. Suitable materials are well known in the art and are described in, for example, U.S. Pat. Nos. 5,185,243, 4,868,104, and 4,959,303, which are incorporated herein by reference. Well-known carriers include glass, polystyrene, polypropylene, polyethylene, dextran, nylon, amylases, natural and modified celluloses, polyacrylamides, agaroses and magnetite. Those skilled in the art will know many other suitable solid supports for binding to the second binding agent, or will be able to ascertain such, using routine experimentation. Binding of ligands and receptors to the support or surface may be accomplished by well-known techniques, readily available in the literature. See, for example, "Immobilized Enzymes," Ichiro Chibata, Halsted Press, New York (1978) and Cuatrecasas, J. Biol. Chem. 245:3059 (1970). Whatever type of solid support is used, it must be treated so as to have bound to its surface a second binding agent. Typical binding agents, as further described below, include ligands, such as biotin, antibodies, intrinsic factor, specifically reactive chemical agents such as sulfhydryl groups that can react with a group on the antigen, and the like. For example, biotin can be covalently bound to spherical glass beads of 0.5–1.5 mm and used to capture a an activator.

Signal producing system ("sps"): one or more components, at least one component being a label, which generate a detectable signal that relates to the amount of bound and/or unbound label, i.e. the amount of label bound or not bound to the compound being detected. The label is any molecule that produces or can be induced to produce a signal, such as a fluorescer, enzyme, chemiluminescer or photosensitizer. Thus, the signal is detected and/or measured by detecting enzyme activity, luminescence or light absorbance.

Suitable labels include, by way of illustration and not limitation, enzymes such as alkaline phosphatase, glucose-6-phosphate dehydrogenase ("G6PDH") and horseradish peroxidase (HRP); ribozyme; a substrate for a replicase such as Q beta replicase; promoters; dyes; fluorescers such as fluorescein, isothiocyanate, rhodamine compounds, phycoerythrin, phycocyanin, allophycocyanin, o-phthaldehyde, and fluorescamine; chemiluminescers such as isoluminol; sensitizers; coenzymes; enzyme substrates; photosensitizers; particles such as latex or carbon particles; suspendable particles; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19–28, and Boguslaski, et al., U.S. Pat. No. 4,318,980, columns 10–14; suitable fluorescers and chemiluminescers are disclosed in Litman, et al., U.S. Pat. No. 4,275,149, at columns 30 and 31; which are incorporated herein by reference. Preferably, at least one sps member is selected from the group consisting of fluorescers, enzymes, chemiluminescers, photosensitizers and suspendable particles.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the sps would then include all the components required to produce a measurable signal, which may include substrates, coenzymes, enhancers, additional enzymes, substances that react with enzymic products, catalysts, activators, cofactors, inhibitors, scavengers, metal ions, specific binding substance required for binding of signal generating substances, and the like. A detailed discussion of suitable signal producing systems can be found in Ullman, et al. U.S. Pat. No. 5,185,243, columns 11–13, which is incorporated herein by reference.

The label is bound to an sbp member which is the analyte, or is capable of directly or indirectly binding the analyte, or is a receptor for the analyte, and includes, without limitation, the analyte; a ligand for a receptor bound to the analyte; a receptor for a ligand bound to the analyte; an antibody that binds the analyte; a receptor for an antibody that binds the analyte; a receptor for a molecule conjugated to an antibody to the analyte; an analyte surrogate capable of binding a receptor for the analyte; a ligand that binds the analyte, etc. Bonding of the label to the sbp member may be accomplished by means of non-covalent bonding as for example by formation of a complex of the label with an antibody to the label or by means of covalent bonding as for example by chemical reactions which result in replacing a hydrogen atom of the label with a bond to the sbp member or may include a linking group between the label and the sbp member. Such methods of conjugation are well known in the art. See for example, Rubenstein, et al., U.S. Pat. No. 3,817,837, which is incorporated herein by reference. Other sps members may also be bound covalently to sbp members. For example, in Ullman, et al., U.S. Pat. No. 3,996,345, two sps members such as a fluorescer and quencher can be bound respectively to two sbp members that both bind the analyte, thus forming a fluorescer-sbp1:analyte:sbp2-quencher complex. Formation of the complex brings the fluorescer and quencher in close proximity, thus permitting the quencher to interact with the fluorescer to produce a signal. This is a fluorescent excitation transfer immunoassay. Another concept is described in Ullman, et al., EP 0,515,194 A2, which uses a chemiluminescent compound and a photosensitizer as the sps members. This is referred to as a luminescent oxygen channeling immunoassay. Both the aforementioned references are incorporated herein by reference.

Ancillary Materials: Various ancillary materials will frequently be employed in the methods in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, or surfactants, particularly non-ionic surfactants, binding enhancers, e.g., polyalkylene glycols, or the like.

As mentioned above, the present invention pertains to methods to detect the presence or amount analyte in a sample suspected of containing the analyte. The methods combine the sensitivity advantage of immunoprecipitation assays with a simplified protocol.

One embodiment of the invention is a method of determining the presence or amount of an analyte in a sample suspected of containing the analyte, said method comprising the steps of: (a) bringing together in an aqueous medium to form a mixture: (i) the sample; (ii) at least one specific binder for the analyte; (iii) a first binding agent coupled to either (1) exogenous analyte or (2) the specific binder for the analyte; (iv) a support comprising a second binding agent; (b) adding an activator to the mixture, wherein the activator binds the first binding agent and the second binding agent of the support to immobilize the first binding agent; and (c) determining the amount of the analyte in the sample by detecting the immobilized first binding agent, the presence or amount thereof being related to the presence or amount of the analyte in the sample.

A critical feature of this invention is that the specific binder for the analyte, the first binding agent and the sample are able to react in the presence of the second binding agent, prior to the addition of the activator which binds the first binding agent to the second binding agent which is immobilized on the solid support. Once the activator is added, the amount of or presence of the first binding agent can be determined, and then related to the amount or presence of the analyte in the sample. This invention enables one to perform the binding steps in an assay mixture in the presence of a specifically activated surface without premature binding of the resulting immune complex to the surface.

One type of assay of the present invention comprises a "One Plate" DELISA protocol which eliminates need for two plates, a transfer step, prewashing of the plate just before use. The total assay time is reduced, e.g., to 3.5 hour.

In the standard DELISA protocol, the primary reaction between the antibody in the sample and the antigen, e.g., bGAD as well as subsequent incubation with the masking compound, e.g., protein A conjugated dextran (PAD), need to be carried out in an inert plate and then transferred to a microtitre plate coated with streptavidin, to get binding to the plate. The methods of the present invention, on the other hand, use microtiter plates which are coated with a first binding agent which permits the entire assay to be performed in the same well. Only when an activator is added to the well, can the antigen, i.e., bGAD, bind in a specific manner. The activator, e.g., streptavidin, with four biotin binding sites, serves as a bridge to bind soluble free bGAD to surface immobilized second binding agents, e.g., bBSA. This modification eliminates the need for two plates and reaction mixture transfer step.

In the modified DELISA assay format of the present invention, the analyte comprises an antibody, the molecule that binds the analyte is an antigen to the antibody, the first binding is coupled to exogenous antigen. In the reaction mixture, the antibody binds the exogenous antigen to form a first binding agent/antigen/antibody complex. Between steps (a) and (b) above, a masking compound that binds the complex and does not bind the antigen when the antigen is not part of the complex is added. In these assays, the activator selectively binds the first binding agent coupled to the antigen, which is not masked by the masking agent, relative to binding the masked complex. The activator also binds the second binding agent. To measure the amount or presence of the analyte, a label bound to a specific binder for the exogenous antigen is added. The amount of label is then detected.

The masking compound prevents the binding of the first binding agent/antigen/antibody complex to the activator and therefore prevents the binding of the complex to the second binding agent, which is coupled to the solid support.

As used herein, the term "selectively binds" means that the activator has the ability to bind preferentially to the first binding agent coupled to the antigen relative to binding the masked first binding agent/antigen/antibody complex. The affinity of the activator for the first binding agent coupled to the antigen will be at least 5-fold and preferably at least 10-fold its affinity for the masked complex. This preferential binding can be kinetic or thermodynamic and will usually be a result of charge repulsion and/or steric hindrance. For example, the masking compound when bound to the complex, may be of such bulk that the activator is unable to bind the first binding agent present in the complex to any significant degree. Therefore, only activator will become bound to the first binding agent coupled to the antigen, which in turn, will then bind to the second binding agent on the solid support.

The specific binder and the masking compounds are sbp members and the binding of the activator to the masked first binding agent/antigen/antibody complex can be better prevented when the masking compound is bound to a soluble polymer or suspendable solid phase. This provides the added advantage that the masking agent bound to the complex does not need to be separated from the medium prior to the addition of the activator because the masking agent and complex does not interfere with the measurement of free antigen.

The sbp member that makes up the masking compound is selected so that it binds the first binding agent/antigen/antibody complex and does not bind the antigen when the antigen is not part of the complex, i.e., the masking compound does not significantly bind to any antigen, free or bound to the first binding agent, present in the medium. The sbp member may also bind other substances present in the sample, e.g., non-analyte antibodies. This is acceptable provided that the masking compound does not bind antigen except when the antigen is bound in the complex.

Suitable sbp members for masking compounds include, without limitation, antibodies to immunoglobulins; complement factor, C1q; rheumatoid factor; protein G and/or protein A. Some of these materials non-selectively bind certain immunoglobulins, for example, antibodies and protein A, and some selectively bind immune complexes, for example, C1q and rheumatoid factor. As noted above, in order to prevent binding of the activator to the first binding agent/antigen/antibody complex, it is preferable, although not necessary, to have the masking compound further comprised of a suspendable solid phase or soluble polymer, i.e., the masking compound is bound to a suspendable solid phase or soluble polymer.

Suitable soluble polymers are linear or preferably branched and include, by way of illustration and not limitation, polysaccharides such as dextran and heparin; polyacrylates, polyacryloyl glucosamine, polyvinylpyrrolidone and the like. The polymers will usually have a molecular weight of at least 10,000 and preferably, the soluble polymers comprising the first binding agent have molecular weights of over 250,000. A preferred polymer comprises dextran.

Suitable suspendable solid phases include, by way of illustration and not limitation, latex, glass particles, particularly porous glass particles, polyacrylamide particles, agarose, SEPHADEX® (Pharmacia Fine Chemicals, Inc.), as well as other particulate phases that are not strictly solids such as liposomes, oil droplets and so forth. Numerous of the aforementioned soluble polymers can be cross-linked to provide suspendable solid phase materials. These materials will usually be particulate and will range in size from 10 nm to 100 nm, preferably from 100 nm to 10 nm.

The first binding agent is an sbp member that is capable of binding an sbp on the activator. For example, the first binding agent can be an antibody, preferably a monoclonal antibody, to the activator, or a portion thereof. The first binding agent may be a receptor, and the activator, or a portion thereof, comprises a ligand that is specific for that receptor. The first binding agent may be ligand to which the activator binds. In such a case, the activator would comprise an antibody to the ligand. Examples of preferred first binding agents include biotin, folate binding protein, fluorescein, haptens (e.g., digoxigenin, dinitrophenol, etc.), carbohydrates, receptors, etc. For example, if the first binding agent is biotin, the activator comprises an entity that specifically binds the biotin, e.g., a sbp member such as avidin, streptavidin, or antibodies to biotin. Alternatively, the first binding agent can be a chemically reactive group that reacts specifically with groups on the activator. For example, the first binding agent could have bromoacetamide groups that can bind specifically with sulfhydryl groups on the activator.

The second binding agent is also a sbp as described above for the first binding pair and is capable of binding an sbp on the activator. The second binding agent can be the same as the first binding pair, or different.

If the second binding agent is the same as the first binding agent, the activator must be able to bind both the first and second binding agents. That is, the activator must be at least bivalent, and preferably multivalent. Examples of multivalent molecules included, but are not limited to, streptavidin and anti-biotin antibodies IgG and IgM. One of ordinary skill in the art can readily select appropriate multivalent molecules for use as activators based upon the teachings herein. For example, if the first and second binding agents are biotin, the activator is preferably a molecule such as streptavidin, anti-biotin IgG or IgM. In another example, in which the first and second binding agents are each a hapten (e.g., fluorescein, digoxigenin, dinitrophenol or others), the activator may comprise a multivalent anti-hapten antibody, preferably IgM. If the first and second binding agents are carbohydrates, the activator may be a lectin, capable of binding both binding agents. When the first and second binding agents are receptors, the activator is preferably a multimeric synthetic peptide. See e.g., Wallace, A., et al., *Pept. Res.,* 7(1), 27–31 (1994). If the activator is not naturally multivalent, e.g., strepavidin, a multivalent molecule can readily be prepared by one of ordinary skill in the art. See e.g., Holliger, WO 9413804 A1 and Libyh, M., et al., *Fr. Blood,* (1997), 90(10), 3978–3983. For example, if the first and second binding agents are folate binding protein, a folate-dextran conjugate can be prepared comprising multiple copies of folate bound to dextran. This conjugate is capable of binding the folate binding protein of both the first and second binding agents.

In assays in which the first binding agent is different from the second binding agent, the activator is a heterofunctional compound that is capable of binding both the first and second binding agents. For example, if the first binding agent is folate binding protein and the second binding agent is fluorescein, the activator is a hybrid conjugate comprising a folate on one end and an antibody to fluorescein one the other end. In another example, if one binding agent is fluorescein and the other is biotin, the activator comprises an anti-fluorescein-streptavidin conjugate. In assays in which the first binding agent comprises a first hapten, hapten A and the second binding agent comprises a second hapten, hapten B, the activator is an anti-A, anti-B bifunctional antibody. Such a bifunctional antibody can be prepared by either genetic engineering or through chemical conjugation of the two antibodies. Preferably the anti-A and anti-B antibodies are monoclonal antibodies or fragments thereof. One of ordinary skill in the art can readily prepare conjugates and heterofunctional compounds that will cross-link the first and second binding agents. See e.g., U.S. Pat. Nos. 3,817,837; 3,996,345; 5,696,264 incorporated herein by reference. See also Cho, B. K., et al., *Bio Conjugate Chem.* (1997) 8(3), 338–346 and Huang, W., et al., *Anal. Chem.,* (1996) 68(9), 1646–1650.

The second binding agent is bound to a soluble polymer or a suspendable or non-suspendable solid phase. The soluble polymers and suspendable supports include polymers such as nucleic acids, proteins, dextrans and polyacrylates; aggregates such as immune complexes; particles such as latex, agarose, SEPHADEX®, dye crystallites, liposomes, oil droplets, metal sols, and the like. The non-suspendable solid phases include bibulous materials such as glass or cellulose paper; plastics such as polystyrene, nylon, polymethacrylate, etc.; silicons, metals such as gold and indium, and the like.

The second binding agent can be attached to the solid support in many ways that are know to the skilled artisan.

For example, when the second binding agent is biotin, the biotin can be attached to the support, e.g., a microtitre plate or beads. This is accomplished by incubating a biotin-BSA conjugate solution in a plastic microtiter well (see e.g., U.S. Pat. No. 5,378,608). Preferably, biotin-BSA is used as described below. Preferably, the method of conjugating the second binding agent to the solid support creates a strong enough bond to prevent the second binding agent from coming off the support.

After addition of the activator, the first binding agent bound to the second binding agent is detected, its presence or amount being related to the presence or amount of the analyte in the sample. In the modified DELISA assay, this relationship is inversely proportional because the higher the concentration of antibodies present in the sample, the lower the amount of free antigen, i.e., the amount of antigen that becomes bound to the second binding agent.

In the modified DELISA assay described above, preferably the antigen bound first binding agent is present in an amount that is less than the expected amount of antibody to be detected. For example, in an assay to determine the amount of an antibody in a serum sample, preferably the molar amount of binding agent conjugated to antigen (binding agent/antigen complex) that is added to the medium containing the sample is usually less than 1 $\mu$M, frequently less than 1 nM, and preferably less than 0.1 nM and is added in an amount not to exceed the highest expected amount of antibodies in the sample. Measurement of free binding agent/antigen complex remaining after binding to the antibodies permits exceptionally sensitive detection of the antibodies.

Preferably a low concentration of the binding agent/antigen complex is used. Although, the lowest practical concentration of the complex will be the lowest concentration that can be detected if the sample has no antibody, it will normally be desirable to use up to 1000 times this minimum detectable concentration, preferably no more than 100 times the minimum detectible concentration. In general, the more complex that is used, the larger the range of antibody concentrations that can be accurately measured and the lower the sensitivity of the assay. One of ordinary skill in the art can readily determine the appropriate concentrations to use based upon the teachings contained herein. See e.g., U.S. Pat. No. 5,561,049.

The present invention eliminates the transfer step of the DELISA assay disclosed in U.S. Pat. No. 5,561,049 and permits the binding reactions, including binding to the solid support, to be carried out in the same reaction, i.e., in the same well of a microtitre plate or test tube. For example, in an assay for measuring GAD antibodies in a blood sample, biotin is used as the first and second binding agent and strepavidin is used as the activator. In such an assay, biotin (i.e., the first binding agent) is coupled to exogenous GAD antigen and biotin (i.e., the second binding agent) is bound to the surface of the support. The sample is mixed with the biotin-GAD conjugate, incubating to provide time for binding to auto-antibody. The masking compound, e.g., protein A-dextran, is then added to bind all the immunoglobulin. However, instead of transferring the mixture to a new streptavidin coated well, streptavidin is then added to the mixture. Because streptavidin is multivalent (four binding sites) it is able to simultaneously bind both the free biotin-GAD conjugate and the biotinylated surface thereby causing the free biotin-GAD conjugate to bind to the surface. The plate is washed. The amount of conjugate that is on the surface is then determined as before, e.g., by measuring the signal produced by a signal producing system. Suitable labels comprise compounds that specifically bind the antigen, i.e., a specific binder. For example, a monoclonal antibody conjugated to horseradish peroxidase (HRP) is added. After a second wash, a chromogenic substrate for HRP, e.g., TMB, is added and the amount of color that develops is determined by known methods, e.g., visual inspection, spectrophometric analysis, etc. Absorbance is inversely proportional to the amount of serum GAD autoantibody.

As aforesaid, because all the reaction occurs within one well or tube, the methods of the present invention eliminate the transfer step required in other methods. In addition, because the solid support is coated with the second binding agent, e.g., biotin, the amount of activator, e.g., strepavidin, that is necessary is diminished. This is an important economic advantage when using strepavidin which is very expensive.

Preferably, the amount of activator that is added to the reaction mixture is less than the total biotin bound to the surface and in the conjugate. More preferably, less than half as many activator equivalents as total first binding agent molecules should be used.

As described above, in certain methods of the present invention, the sample may be washed after addition of the members of the signal producing system, e.g., after addition of a monoclonal antibody conjugated to HRP, and before addition of the enzyme substrate. However, in other methods of this invention, this wash step is eliminated. Such methods use signal producing systems that produce a detectable signal in a homogeneous format, i.e., which does not require these wash steps. For example, the scintillation proximity assay (SPA) does not require a separation step. See Linace, P., et al., *Methodol. Surv. Biochem. Anal.*, (1992) 22 (Bioanal. Approaches Drugs, Inc. Anti-Asthmatics Metab.), 325–6. This method involves the use of a SPA reagent comprising beads made from yttrium silicate coated with a substance capable of fluorescence (fluor). Another member of the signal production system comprises a radiolabeled ligand that emits $\beta$-particles when in close proximity to the fluor, producing light that can be detected in a scintilation counter. Thus, when the radioligand is bound to the solid surface, it produces a detectable signal that is indicative of the amount of analyte in the sample. Radioligand not bound to the solid support is too far from the fluor to produce a signal. In another example, electrocherniluminescent organometallic compounds can be used to detect and quantify analytes in homogeneous binding assays. See U.S. Pat. No. 5,731,147. Other useful signal producing systems are readily available to one of ordinary skill in the art.

The invention further relates to competitive assays. In a competitive assay format either the specific binder or the exogenous analyte is detectable and the first binding agent is coupled to exogenous analyte. The determining step comprises detecting the detectable specific binder or exogenous analyte. For example, in a particular assay, the analyte of interest is an antigen, e.g., digoxin, and the specific binder to the analyte is a molecule that specifically binds the antigen, preferably an anti-digoxin antibody, or a fragment thereof. The specific binder comprises a component of a signal producing system, such as an enzyme or other appropriate label. In this type of assay, the first binding agent is coupled to exogenous antigen. For example, biotin, a first binding agent would be coupled, by methods known in the art to digoxin. Conjugates comprising a member of a signal producing system, first binding agent, e.g., biotin, and antigen can be prepared by methods known in the art, e.g., U.S. Pat. No. 4,506,009. The labeled specific binder is added to the sample suspected of containing the analyte and either at the same time, or subsequently, the first binding agent is also added. The analyte in the sample competes with the analyte that is coupled to the first binding agent for binding with the specific binder, and the analyte coupled to the first binding agent forms a complex with the specific binder in an amount that is proportional to the amount of analyte in the sample. This reaction occurs in the presence of the second binding agent immobilized on a solid support. As described above, the second member can be any type of ligand, receptor, antigen or antibody, provided it does not bind the first binding agent, or the analyte, prior to activation. In a preferred competitive assay, the second binding agent is biotin.

In these assays, an activator is then added that binds the first binding agent in the complex and the second binding agent. As described above, the activator can have many forms, depending on the nature of the first and second binding agents. In the above example, where both the first and second binding agents comprises biotin, the activator is preferably a multivalent compound that can bind biotin at more than one site. Preferred activators include avidin, streptavidin, anti-biotin antibody. The activator binds the first binding agent bound to the antigen, e.g., biotin, that has competed with the sample antigen for binding with the specific binder, e.g., antibody, and the second binding agent bound to the solid surface. Thus, the reaction mixture does not need to be transferred to another well or test tube prior to being coupled to the solid support. The methods of the present invention enable the above reaction to occur in one tube or reaction well.

In a preferred competitive assay, the sample suspected of containing an antigen is mixed with anti-antigen bound to an enzyme (an anti-antigen enzyme conjugate) in a well coated with the second binding agent, e.g., biotin. The reaction is incubated for the required time. Antigen coupled to the first binding agent, e.g., biotin, is added to the reaction mixture. The reaction is allowed to incubate for an amount of time that is readily ascertained by one of ordinary ski in the art. The activator, e.g., streptavidin is added following the required incubation. The amount of streptavidin added is determined by the amount of biotin coated on the solid surface and the amount of biotin labeled antigen added. The reaction mixture is removed and the microtiter well maybe washed. Enzyme substrate is added and the enzyme product is detected. The amount of label bound to the solid surface can be directly measured or the amount of antigen on the surface can be indirectly measured by the binding of a detectably labeled antibody to the analyte. Enzyme activity is proportional to bound anti antigen antibody, thus inversely proportional to the amount of antigen in the sample.

In this example, the sample, labeled or unlabeled biotinylated analyte, and antibody to the analyte can be incubated in a biotinylated well followed by addition of streptavidin to cause the free biotinylated analyte to bind to the surface. The biotinylated analyte preferably does not bind simultaneously to the antibody and streptavidin.

In the case of competitive assays, the specific binder preferably has the same affinity for the exogenous antigen that is bound to the first binding agent as for the antigen in the sample. When the affinity of the specific binder, i.e., antibody, to the sample antigen is the same for the antigen bound to the first binding agent, there is true competition. In certain embodiments it may be desirable to have a competitive assay that is a displacement assay. In such an embodiment, the specific binder has a greater affinity for the sample antigen than for the antigen that is coupled to the first binding agent. In this type of assay, the specific binder can be complexed to the antigen coupled to the first binding agent prior to addition of this complex to the sample. The antigen in the sample would then displace the exogenous antigen bound to the first binding agent relative to the amount of antigen present in the sample.

Preferably the specific binder, e.g., antibody to the analyte of interest, will be specific for a particular site on the antigen that is the same on the sample antigen as well as the exogenous antigen coupled to the first binding agent. Preferred specific binders include antibodies, more preferably, monoclonal antibodies, or fragments thereof, to the antigen of interest. Other preferred specific binders include receptors to the antigen. The coupling of the first binding agent to the exogenous antigen should not interfere with the binding of the specific binder and the binding of the specific binder to the exogenous antigen should not interfere with the binding of the first binding agent to the activator.

The above description uses the term "antigen" to refer to the analyte of interest. However, it will be recognized that any analyte of interest can be so determined, e.g., ligands or other molecules that bind to a specific receptor, such as such as folate or receptors.

For the competitive type assays, preferably the first binding agent, bound to exogenous antigen, is present in an amount that will not exceed the capacity of the binding sites on the solid support. The specific binder is preferably present in an amount that does not exceed the ability to bind the first binding agent/antigen complex. Preferably, the antigen is not present in excess, because this may decrease the sensitivity of the assay.

Also within the scope of the invention are sandwich-type immunoassays in which a first and second specific binder to the analyte, e.g., antibodies, are combined with the sample to form a specific binder:analyte:specific binder complex wherein one of the specific binders is conjugated to a first binding agent and the other with a detectable label in the form of a member of a signal producing system. Following the binding reaction, the activator is added thereby causing the complex to bind to the surface of the reaction well which has been precoated with a second binding agent. The amount of detectable label bound to the surface is then measured. The amount of label is directly proportional to the amount of antigen in the sample. In these assays the first and second specific binders preferably bind to two different epitopes on the analyte, so that they do not compete for the same binding site. The order of addition of the two specific binders to the sample can be sequential, or simultaneous. It may be desirable to allow the reaction mixture containing the specific binders and the sample to incubate for a period of time to allow for complete binding of the analyte by the two specific binders before the addition of the activator. After the activator is added and allowed to react, the solution may be washed to remove unbound label. Useful washing techniques are readily known by one of ordinary skill in the art. If the label is an enzyme, the substrate for the enzyme can then be added and the signal measured.

The sandwich type assays of the present invention are useful for determining the presence of or amount of any analyte that can be determined by presently known sandwich assays. Examples include, but are not limited to, bone specific alkaline phosphatase, haptens, proteins, polypeptides, hormones such as insulin and human thyroid stimulating hormone (HTSH), gamma globulins, allergens, viruses, virus subunits, bacteria, toxins such as those associated with tetanus and with animal venoms, and even some drugs. Among the specific antigens which may be assayed by the process of the present invention may be mentioned carcinoembryonic antigen (CEA), hepatitis A and B, hepatitis Non A/Non B, IgE and alphafetoprotein. Antibobodies to these analytes are either available in the art or readily obtainable by one of ordinary skill in the art. See e.g., U.S. Pat. Nos. 5,525,473 and 5,589,574.

Another aspect of the present invention is a kit for detecting the presence of or determining the amount of analyte in a fluid sample. The reagents of the methods of this invention are stable with long shelf-lives and are inexpensive to manufacture and use. Therefore, these reagents are amenable to a kit formulation. A kit of the present invention comprises the components necessary for performing the methods of this invention in packaged combination. A kit of the present invention comprises (1) at least one specific binder for the analyte; (2) a first binding agent coupled to either (a) exogenous analyte or (b) the specific binder for the analyte; (3) a support comprising a second binding agent; and (4) an activator that binds the first binding agent and the second binding agent of the support to immobilize the first binding agent.

The specific components of the kit can be selected by one of ordinary in the art in accorddance with the type of assay to be performed. For example, in a kit for performing a DELISA assay where the analyte is an antibody, the specific binder is an antigen to the antibody, the first binding agent is biotin which is coupled to antigen, the second binding agent comprises biotin which is bound to the walls of a container, and the activator comprises streptavidin.

In a kit for performing a modified DELISA assay, the kit further comprises a masking compound bound to a suspendable solid phase or soluble polymer. The suspendable solid phase is preferably a particle comprised of a material selected from the group consisting of polymers, ceramic and glass. Preferred masking compounds include antibodies to immunoglobulins, complement factor C1q, rheumatoid factor, protein G and protein A, which can be selected depending on the analyte to be tested.

The kits of the present invention may also include at least one member of a signal producing system, if desired. At least one of said signal producing system members is selected from the group consisting of fluorescers, enzymes, chemiluminescers, photosensitizers and suspendable particles and can be selected as described above.

A preferred kit in accordance with the present invention useful for the detection of GAD autoantibodies comprises GAD antigen bound to biotin as the first binding agent. The kit also comprises a solid support, such as a microtitre plate that is coated with BSA-biotin, as the second binding agent. Protein-A bound to a soluble polymer, such as dextran, would be included as the masking agent. Streptavidin would be included as the activator. An anti GAD monoclonal Ab-HRP conjugate is included.

The amounts of each of the components would depend on the analyte of interest as well as the nature of the sample to be measured. One skilled in the art is capable of making such a determination based upon methods known in the art and the disclosure contained herein. It is understood in the art that components and reagents can be supplied to be used in kits according to any of a number of different formats.

Under appropriate circumstances one or more of the reagents in the kit can be provided in solution or as a dry powder, usually lyophilized, including excipients, which on dissolution will provide for a reagent solution having the appropriate concentrations for performing a method or assay in accordance with the present invention. The kit is not limited by the form of the components, i.e., powder, liquid or tablet. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. As a matter of convenience, the reagents employed in the present invention can be provided in predetermined amounts. The kit can also contain written instructions on how to use the reagents and/or how to perform a particular assay, for example, in the form of a package insert.

Appropriate reaction conditions are chosen for carrying out the methods in accordance with the present invention. The following description sets forth suitable conditions, which are subject to modification by those skilled in the art depending on the specific reagents and assay protocol chosen for any particular application. For example, the methods of this invention can be applied to numerous types of assays such as heterogeneous or homogeneous, and the conditions and reagents used will be selected accordingly.

The sample, preferably in a suitable medium, can be examined directly or may be pretreated before the sample is added to the assay medium. Pretreatment can render the analyte of interest more readily available to one or more of the assay reagents or more readily detectible by reducing interference in the assay by removing any unwanted materials. The sample may be pretreated to separate or lyse cells; precipitate, hydrolyse or denature proteins; hydrolyze lipids; or the like. Such pretreatment may include, without limitation: centrifugation; treatment of the sample with an organic solvent, for example, an alcohol, preferably an alcohol having less than about 7 carbon atoms such as methanol; and treatment with detergents.

The concentration of the analytes to be assayed will generally vary from about 0 to about $10^{-17}$ M, more usually from about 0 to about $10^{-14}$ M, most usually from about $10^{-5}$ to about $10^{-14}$ M. The relative amounts of the various reagents used in the assay and packaged in the kits described below can be varied widely to provide for concentrations of the reagents that substantially optimize the reactions that need to occur during the present method and to further substantially optimize the sensitivity of any assay performed. For example, considerations such as the tradeoff between sensitivity and the assay range, the particular detection technique, and the concentration of the analyte will determine the concentration of antigen used, as explained above, and will normally determine the concentration of the other reagents also. In addition, the final concentration of each of the reagents will normally be determined empirically to optimize the sensitivity of the assay over the range of interest.

In carrying out the method of this invention, preferably an aqueous buffered medium at a moderate pH will be employed, generally that which provides optimum assay sensitivity. The aqueous medium may be solely water or may include a cosolvent such as an oxygenated organic solvent of from 1–6, more usually from 1–4 carbon atoms, including alcohols, ethers and the like. Usually the cosolvent will be present in less than about 70 weight percent, more usually, in less than about 30 weight percent.

In assays in accordance with the present invention, the pH for the medium will usually be in the range of about 5–10, preferably, in the range of about 7–9. The pH is chosen so as to maintain a significant level of binding between sbp members, while optimizing signal producing proficiency. In some instances, a compromise will be made between these two considerations.

Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the method and usually constant temperatures during the period of the measurement, particularly for rate determinations. The temperature may vary with the step being undertaken, with the temperatures ranging from 5°–50° C., usually from about 15°–40° C. Incubation temperatures will normally range from 5°–45° C., more usually from 15°–40° C. Temperatures during measurements will generally range from 10°–50° C., more usually from 15°–40° C.

While the order of addition of the various reagents may depend on the type of assay format used, numerous protocols can be devised by using various techniques for timed release of reagents. Where such procedures are not employed, it will usually be preferable to combine the sample and first binding agent, before or nearly simultaneously with the specific binder for the analyte. Where the activator can bind the antigen:antibody complex without binding the uncomplexed immunoglobulins, the order of addition of these reagents is unimportant. Addition of the activator must be subsequent to the first two additions unless a means is provided for the timed release of this agent. Other reagents capable of binding the antigen can be added at any time but are preferably added nearly simultaneously with or subsequent to addition of the activator. The timing of the addition of other reagents may vary widely.

Optionally, one or more incubation steps may be involved after each reagent addition, generally ranging from about 30 seconds to 6 hours, more usually from about 2 minutes to 1 hour. In addition, the assay may involve one or more wash steps, as needed.

The following examples are provided to more clearly illustrate the aspects of the invention and are not intended to limit the scope of the invention. The examples are merely illustrative of the qualitative, semi-quantitative and quantitative assay protocols in which the method of this invention can be used for determining the presence or amount of antibodies in a sample. The signal detected in these methods is compared to a standard or control, having a known concentration of antibodies.

EXAMPLES

Example 1

Determination of Anti GAD Auto Antibody in Sera of IDDM (Insulin Dependent Diabetes Melitus)

The following example describes a simplified protocol for the previously described DELISA assay for the detection of GAD auto antibody in serum (U.S. Pat. No. 5,561,049). The simplified depletion based assay protocol as described provides the following advantages: A. eliminates the need for incubation on two wells; B. eliminates one wash step; C. shorter total assay time; and D. provides a surface modification that is stable and thus does not require a wash step prior to initiation of the test (required in the previously described procedure for the removal of binder which detaches from the solid surface upon storage).

The following materials and equipment were used in the examples described below.

Nunc U8 maxisorp round bottom 96-well microtiter plate/strips, Cat#475078, Batch#012758.

Costar High Binding Flat Bottom 96-well microtiter plate, Cat#9018, Lot#B23C4064.

Biotinylated BSA from Pierce Chemical Co., Rockford, Ill., USA. Cat#29130, Lot#95062965, 25 mg as freeze-dried powder with 8 moles of biotin per mole of BSA.

Streptavidin: a solution at 21.8 mg/mL was aliquoted and stored at −20° C.

DELISA reagents were prepared as described in U.S. Pat. No. 5,561,049.

Protein A coupled to Dextran Aldehyde (PrA-DxA1) (in-house), Lot#950062 (as described in U.S. Pat. No. 5,561,049).

Universal Reagent Kits (URK) from DBI Productions, Cupertino, Calif., USA.

BSA (Protease free fraction V) from Sigma Chemical Co., St. Louis, Mo.,USA, Cat#3294, Lot#73H0391.

Pefabloc SC from PentapharmAG, Basel, Switzerland. Lot#1619/399

Aprotinin (Solution at 229,500 KIU/mL) from PentapharmAG, Basel, Switzerland. Lot#5420/073

Gentamicin (5% solution) from Gibco/BRL, Gaithersburg, Md., USA, Cat#15750-011, Lot#15K3452.

MicroTrak (Dade Behring Inc., Syva Product Group) Plate Washer and Reader

Single or Multichannel Programmable Proline Pipettes from Biohit

Preparation of bBSA Coated Plate

To a vial containing lyophilized biotinylated bovine serum albumin (bBSA) powder, as per the manufacturer's instructions, 14.5 mL distilled water was added and dissolved at 4° C. (2–8° C.) by rotating on a shaker for 15–30 minutes or until the solution looks clear. Protein concentration was measured by BCA method (Pierce BCA kit, Cat#23225) using BSA as a standard. The solution was determined to be at 1.7 mg/mL and was aliquoted into small (1.0 mL) volumes and stored at −20° C. for future use.

Biotinylated BSA solution was diluted 1 to 10 in 0.1 M Potassium phosphate (KPi) buffer, pH 8.1, in three sequential steps (i.e., a total of 1000-fold dilution) to obtain 1.7 $\mu$g/mL. Just prior to coating Nunc plates, 7.05 mL of the diluted (1.7 $\mu$g/mL) bBSA was added to 112.95 mL KPi buffer and mixed gently to avoid frothing. This working solution is at 100 ng/mL and sufficient to coat 10 plates.

Using a multichannel pipette, 0.1 mL of working solution of bBSA was added to wells of Nunc microtiter plate. The plates were covered with a lid and incubated in humidified incubator at 37+2° C. for 3 h. Plates were then washed (300 $\mu$L per well, 5 times) with MicroTrak wash buffer on MicroTrak washer.

The plates were dried at 30–37° C. in a vacuum oven (SP/Baxter, Model#N7595-1) hooked up to house vacuum. A beaker of phosphorous pentoxide (Mallinckrodt, Cat#6612, Lot#6612KMSL) was kept in the oven to absorb moisture. Following drying for 30–40 minutes, plates were removed, packaged and sealed individually in an aluminum bag with a DRYRITE™ pouch. Plates were typically stored at 2–8° C. unless otherwise mentioned.

Preparation of Streptavidin Working Reagent

A diluent for streptavidin (Sav) working reagent was prepared with the following composition:

20 mM Potasium Phosphate buffer, pH 7.0 containing 150 mM NaCl 1 mM EDTA 1 mM Pefabloc 0.1% Triton-X-100

0.1% Gentamicin (i.e., 50 µg/mL final concentration)

0.0033 TIU/mL Aprotinin solution 1 mg/mL BSA

Sav at 21.8 mg/mL (363.3 µM) was diluted 1 to 1000 to get 0.363 µM concentration. To 246 mL of Sav diluent, 4.132 mL of 0.363 µM Sav was added and gently mixed to get a final Sav concentration 6 nM in the working reagent. A 25 µL aliquot contains 0.15 pmol Sav/well. This reagent was aliquoted and stored at 2–8° C.

Two Plate' Standard DELISA

Duplicate/triplicate wells in polypropylene 96-well microtiter plate were set up. To each well was added 25 µL calibrator or test sample.

A stock biotinylated glutamic acid decarboxylase, GAD65 (bGAD) diluent was prepared according to the teaching of U.S. Pat. No. 5,551,049. The working bGAD solution was prepared in a disposable reagent reservoir by adding 3.15 mL of stock bGAD diluent into the tray and then adding 0.35 mL of stock bGAD. This solution was mixed thoroughly by pipetting up and down with a 5 mL pipette. These volumes are for a full plate and can be changed proportionately for a small or a large assay.

Using a multichannel pipette, 25 µL of bGAD solution was added to bottom of the well and mixed with sera using multichannel pipette by gently drawing up and down twice. Pipette tips were changed after each mixing. The microtiter plate was covered with mylar seal tape and incubate for 2 hours at room temperature (RT) (22–24° C.).

Using a multichannel pipette, 50 µL ProteinA-conjugated dextran Reagent (PAD) was added from a reagent reservoir to serum/bGAD to the bottom of the well and mixed as in step 3. Pipette tips were changed after each mixing. The plates were covered with mylar tape, and incubated for 1 hour at RT.

A streptavidin-coated plate was removed from its pouch and prewashed using one cycle of the Syva MicroTrak plate washer (5×300 µL).

Using a multichannel pipette, 80 µL of the reaction mix (bGAD/serum/PAD) was transferred from the first polypropylene plate (Step 4) to the prewashed streptavidin-coated plate. Pipette tips were changed after each transfer. The plate was covered with the plastic cover. The covered plate was incubated for 1 hr at RT while shaking gently on a microtiter plate shaker.

The microtiter plate was washed as above. Using a multichannel pipette, 100 µL MAb-HRP Conjugate solution was added from a reagent reservoir. The plate was incubated at RT for 1 hour while shaking.

The microtiter plate was washed as above. 6.0 ml each of TMB and $H_2O_2$ solutions (HRP substrates from KPL or URK kit) were mixed well in a reagent reservoir. Using a multichannel pipette, 100 µL of the mixture was added to each well from a reagent reservoir. Color was allowed to develop for 30 min at RT and stopped with 100 µL of stop solution (1N $H_2SO_4$ from Fisher).

The color was read at 450 nm on the Syva MicroTrak plate reader (with 630 nm as the reference wavelength).

One Plate' DELISA Protocol

Duplicate/triplicate wells were set up in bBSA coated Nunc U8 maxisorp 96-well microtiter plate. 25 µL calibrator or test sample was added to each well.

The working bGAD solution was prepared in a disposable reagent reservoir by adding 3.15 mL of stock bGAD diluent into the tray and then adding 0.35 mL of stock bGAD. The solution was mixed thoroughly by pipetting up and down with a 5 mL pipette. These volumes are for a full plate and can be changed proportionately for a small or a large assay.

Using a multichannel pipette, 25 µL of bGAD solution was added to bottom of the well and mixed with sera using multichannel pipette by gently drawing up and down twice. Pipette tips were changed after each mixing. The microtiter plate was covered with a lid and incubated for 2 hr (or indicated time for a specific expt.) at RT (22–24° C.).

Using a multichannel pipette, 25 µL ProteinA-Reagent (PAD) was added from a reagent reservoir to serum/bGAD to the bottom of the well and mixed as in step 3. Pipette tips were changed after each mixing. The plate was covered with a lid and incubated for 1 hour at RT.

Using a multichannel pipette, 25 µL Sav working reagent from a reagent reservoir was added to the bottom of the well containing serum/bGAD/PAD and mixed as in step 3. Pipette tips were changed after each mixing. The plate was covered with a lid and incubated for 1 hour at RT while shaking on a platform shaker.

The microtiter plate was washed (5 times 300 µL). Using a multichannel pipette, 100 µL MAb-HRP Conjugate solution was added from a reagent reservoir. The mixture was incubated at RT for 1 hour while shaking.

The microtiter plate was washed as in the previous step. 6.0 ml each of TMB and $H_2O_2$ solutions (HRP substrates from KPL or URK kit) was mixed well in a reagent reservoir. Using a multichannel pipette, 100 µL of the mixture was added to each well from a reagent reservoir. Color was allowed to develop for 30 min at RT, and stopped with 100 µL of stop solution (1N $H_2SO_4$ from Fisher).

The plate was read at 450 nm on the Syva MicroTrak plate reader (with 630 nm as the reference wavelength).

Optimization of bBSA Coating

Sav coated plates were manufactured and provided by Syva. These plates were coated with Sav at 500 ng/well/0.1 ml DPBS for 4 days at 2–8° C. The plates were then washed with deionized water, dried at 50±5° C. for 5 min, placed in a foil pouch with a bag of Dryrite, sealed and stored at 2–8° C. Because passively adsorbed Sav "peels" off under this condition, it is necessary to prewash plate on MicroTrak washer just before use in the assay. The use of unwashed plate decreased the signal by an unacceptable 80–90% (Table 1A).

High protein binding 96-well microtiter plates from Nunc #475078 U8 maxisorp and Costar #9018 plates were prepared by coating bBSA at 250 ng/well and 10 ng/well. The stored plates were either washed just prior to use in the assay or used unwashed. The one plate DELISA procedure is similar to the standard DELISA protocol except that bBSA coated plates are used and soluble Sav is added to the reaction mixture in place of the transfer step.

If there were no loss of passively coated bBSA following the plate preparation and storage, then assay signal and modulation in the washed and unwashed plates will remain-comparable. In the plates coated with bBSA at 250 ng/well (Nunc, Table 1B and Costar, Table 1D), the signal ratio (unwashed/washed) is 0.3–0.4, indicating about 60–70% decrease. This means that "peeled off" bBSA binds Sav-bGAD and the ternary complex washes off in the next step, resulting in decreased signal.

In plates coated at 10 ng/well (Nunc, Table 1C and Costar, Table 1E), the ratio is 1.0, indicating no loss of signal. At low coating concentration, all of the input bBSA anchors well onto the surface giving a stable layer. Based on these results, for future experiments, Nunc plates coated at 10 ng/well were prepared.

brators and 19 sera. (Table 2, A and B). The results show a good correlation between the two methods employing the same reagents. The results also show good reproducibility of the two methods. Table 2A shows a comparison of results

TABLE 1A

Two Plate DELISA
(Nunc plate coated with Sav at Cupertino, plate lot#8K718.G1)

| Sample | Rel GADab | A450 | A450 | WASHED AveA450 | Normalized SC1 as 100% | A450 | A450 | UNWASHED AveA450 | Normalized SC1 as 100% | RATIO Unwash/Wash |
|---|---|---|---|---|---|---|---|---|---|---|
| SC1 | 0 | 0.847 | 0.868 | 0.858 | 100.0 | 0.13 | 0.13 | 0.131 | 100.0 | 0.2 |
| SC2 | 1 | 0.604 | 0.610 | 0.607 | 70.8 | 0.09 | 0.09 | 0.088 | 67.0 | 0.1 |
| SC3 | 2 | 0.455 | 0.466 | 0.461 | 53.7 | 0.08 | 0.07 | 0.070 | 53.6 | 0.2 |
| SC4 | 4 | 0.262 | 0.266 | 0.264 | 30.8 | 0.05 | 0.04 | 0.048 | 36.8 | 0.2 |
| SC5 | 16 | 0.042 | 0.045 | 0.044 | 5.1 | 0.02 | 0.02 | 0.022 | 16.9 | 0.5 |

TABLE 1B

One Plate DELISA
(Nunc#475078, U8 maxisorp coated with bBSA, plate lot#12996, BBSA(Pierce) @ 250 ng/well/0.1 mL, Sav(Art#3617-24) at 220 fmol/well)

| Sample | Rel GADab | A450 | A450 | WASHED AveA450 | Normalized SC1 as 100% | A450 | A450 | UNWASHED AveA450 | Normalized SC1 as 100% | RATIO Unwash/Wash |
|---|---|---|---|---|---|---|---|---|---|---|
| SC1 | 0 | 0.535 | 0.649 | 0.592 | 100.0 | 0.15 | 0.19 | 0.173 | 100.0 | 0.3 |
| SC2 | 1 | 0.424 | 0.579 | 0.502 | 84.7 | 0.12 | 0.15 | 0.131 | 75.7 | 0.3 |
| SC5 | 2 | 0.354 | 0.438 | 0.396 | 66.9 | 0.12 | 0.14 | 0.126 | 72.5 | 0.3 |
| SC4 | 4 | 0.201 | 0.283 | 0.242 | 40.9 | 0.09 | 0.11 | 0.102 | 58.7 | 0.4 |
| SC5 | 16 | 0.096 | 0.117 | 0.107 | 18.0 | 0.07 | 0.08 | 0.077 | 44.2 | 0.7 |

TABLE 1C (BBSA(Pierce) @ 10 ng/well/0.1 mL)

| SC1 | 0 | 0.617 | 0.673 | 0.645 | 100.0 | 0.66 | 0.69 | 0.675 | 100.0 | 1.0 |
|---|---|---|---|---|---|---|---|---|---|---|
| SC2 | 1 | 0.446 | 0.460 | 0.453 | 70.2 | 0.46 | 0.46 | 0.459 | 68.1 | 1.0 |
| SC3 | 2 | 0.366 | 0.373 | 0.370 | 57.3 | 0.37 | 0.36 | 0.364 | 54.0 | 1.0 |
| SC4 | 4 | 0.218 | 0.215 | 0.217 | 33.6 | 0.23 | 0.21 | 0.219 | 32.4 | 1.0 |
| SC5 | 16 | 0.071 | 0.071 | 0.071 | 11.0 | 0.07 | 0.08 | 0.070 | 10.4 | 1.0 |

TABLE 1D (Costar #9018 coated with bBSA, plate lot #12996. bBSA(Pierce) @ 250 ng/well/0.1 mL)

| SC1 | 0 | 0.762 | 0.965 | 0.864 | 100.0 | 0.28 | 0.3 | 0.289 | 100.0 | 0.3 |
|---|---|---|---|---|---|---|---|---|---|---|
| SC2 | 1 | 0.527 | 0.649 | 0.588 | 68.1 | 0.25 | 0.22 | 0.233 | 80.6 | 0.4 |
| SC3 | 2 | 0.484 | 0.563 | 0.524 | 60.6 | 0.18 | 0.21 | 0.194 | 67.1 | 0.4 |
| SC4 | 4 | 0.283 | 0.333 | 0.308 | 35.7 | 0.13 | 0.11 | 0.124 | 42.7 | 0.4 |
| SC5 | 16 | 0.091 | 0.123 | 0.107 | 12.4 | 0.07 | 0.08 | 0.078 | 26.8 | 0.7 |

TABLE 1

(bBSA(Pierce) @ 10 ng/well/0.1 mL)

| SC1 | 0 | 0.519 | 0.611 | 0.565 | 100.0 | 0.57 | 0.64 | 0.603 | 100.0 | 1.1 |
|---|---|---|---|---|---|---|---|---|---|---|
| SC2 | 1 | 0.380 | 0.386 | 0.383 | 67.8 | 0.44 |  | 0.435 | 72.2 | 1.1 |
| SC3 | 2 | 0.275 | 0.272 | 0.274 | 48.4 | 0.33 | 0.29 | 0.311 | 51.5 | 1.1 |
| SC4 | 4 | 0.169 | 0.181 | 0.175 | 31.0 | 0.18 | 0.18 | 0.180 | 29.8 | 1.0 |
| SC5 | 16 | 0.056 | 0.057 | 0.057 | 10.0 | 0.06 | 0.06 | 0.056 | 9.2 | 1.0 |

Comparison of One-plate and Two-plate DELISA Procedures

Nunc bBSA coated plates were used unwashed for comparing the performance in DELISA employing serum calibrators with one plate (No transfer) & two plates (with transfer) methods. DELISA was performed with serum calibrators, control and diabetic sera. The standard DELISA protocol assay time was 5.5 h.

TABLE 2A

| Sample | Rel GADab | One-plate (bBSA coated) No transfer method | | | | | Two plate (Sav coated) Transfer step method | | | | |
|---|---|---|---|---|---|---|---|---|---|---|---|
| | | A450 | A450 | Ave A450 | AvDev | % CV | A450 | A450 | Ave A450 | AvDev | % CV |
| SC1 | 0 | 1.438 | 1.335 | 1.387 | 0.052 | 3.7 | 1.705 | 1.654 | 1.680 | 0.026 | 1.5 |
| SC2 | 1 | 1.056 | 1.031 | 1.044 | 0.013 | 1.2 | 1.203 | 1.185 | 1.194 | 0.009 | 0.5 |
| SC3 | 2 | 0.778 | 0.750 | 0.764 | 0.014 | 1.8 | 0.886 | 0.879 | 0.883 | 0.004 | 0.4 |
| SC4 | 4 | 0.440 | 0.398 | 0.419 | 0.021 | 5.0 | 0.422 | 0.431 | 0.427 | 0.005 | 1.1 |
| SC5 | 16 | 0.104 | 0.092 | 0.098 | 0.006 | 6.1 | 0.062 | 0.036 | 0.049 | 0.013 | 26.5 |
| CS4 | | 0.097 | 0.245 | 0.171 | 0.074 | 43.3 | 0.049 | 0.044 | 0.047 | 0.003 | 5.4 |
| CS6 | | 0.996 | 0.959 | 0.978 | 0.019 | 1.9 | 0.753 | 0.790 | 0.772 | 0.019 | 2.4 |
| CS9 | | 1.920 | 1.843 | 1.882 | 0.039 | 2.0 | 1.766 | 1.771 | 1.769 | 0.002 | 0.1 |
| CS10 | | 1.502 | 1.457 | 1.480 | 0.023 | 1.5 | 1.426 | 1.583 | 1.505 | 0.079 | 5.2 |
| CS19 | | 0.403 | 0.446 | 0.425 | 0.022 | 5.1 | 0.304 | 0.373 | 0.339 | 0.035 | 10.2 |
| CS23 | | 0.017 | 0.021 | 0.019 | 0.002 | 10.5 | 0.016 | 0.016 | 0.016 | 0.000 | 0.0 |
| CS28 | | 1.609 | 1.814 | 1.712 | 0.103 | 6.0 | 1.726 | 1.730 | 1.728 | 0.002 | 0.1 |
| CS29 | | 0.049 | 0.050 | 0.050 | 0.001 | 1.0 | 0.017 | 0.016 | 0.017 | 0.001 | 3.0 |
| CS30 | | 1.071 | 1.126 | 1.099 | 0.028 | 2.5 | 1.088 | 1.018 | 1.053 | 0.035 | 3.3 |
| CS31 | | 1.109 | 0.919 | 1.014 | 0.095 | 9.4 | 0.856 | 0.567 | 0.712 | 0.145 | 20.3 |
| CS34 | | 1.460 | 1.625 | 1.543 | 0.083 | 5.3 | 1.507 | 1.515 | 1.511 | 0.004 | 0.3 |
| CS40 | | 0.814 | 0.891 | 0.853 | 0.039 | 4.5 | 0.787 | 0.821 | 0.804 | 0.017 | 2.1 |
| CS44 | | 0.167 | 0.384 | 0.276 | 0.109 | 39.4 | 0.038 | 0.022 | 0.030 | 0.008 | 26.7 |
| CS55 | | 0.952 | 1.028 | 0.990 | 0.038 | 3.8 | 0.930 | 0.997 | 0.964 | 0.034 | 3.5 |
| PBB1 | | 1.861 | 1.742 | 1.802 | 0.060 | 3.3 | 1.941 | 1.986 | 1.964 | 0.023 | 1.1 |
| PBB2 | | 1.698 | 2.376 | 2.037 | 0.339 | 16.6 | 1.724 | 1.679 | 1.702 | 0.023 | 1.3 |
| PBB3 | | 1.663 | 1.686 | 1.675 | 0.012 | 0.7 | 1.583 | 1.605 | 1.594 | 0.011 | 0.7 |
| PBB4 | | 1.522 | 1.669 | 1.596 | 0.074 | 4.6 | 1.831 | 1.867 | 1.849 | 0.018 | 1.0 |
| KH | | 1.312 | 1.389 | 1.351 | 0.039 | 2.9 | 1.710 | 1.625 | 1.668 | 0.043 | 2.5 |

SC = Serum calibrators
CS = patient sera
PBB = Peningula Blood Bank, control sera
KH = A control serum Table 2B shows a comparison of results with one plate (No transfer) & two plates (with transfer) methods. DELISA performed with serum calibrators, control and diabetic sera. Reagents: bGAD, bGAD diluent, serum calibrators stored at −70° C., Sav plate (lot#895), PAD, DxA1 (lot#950062), Conjugate (lot#295), bBSA plate (lot#2896) at 4° C., substrate & stop solutions (Syva, URK lot#8K209UL) at 4° C. The standard DELISA protocol had an assay time of 5.5 h.

TABLE 2B

| Sample | Rel GADab | One-plate (bBSA coated) No transfer method | | | | | Two plate (Sav coated) Transfer step method | | | | |
|---|---|---|---|---|---|---|---|---|---|---|---|
| | | A450 | A450 | Ave A450 | AvDev | % CV | A450 | A450 | Ave A450 | AvDev | % CV |
| SC1 | 0 | 1.175 | 1.232 | 1.204 | 0.029 | 2.4 | 1.42 | 1.439 | 1.430 | 0.010 | 0.7 |
| SC2 | 1 | 0.822 | 0.877 | 0.850 | 0.028 | 3.2 | 0.949 | 0.970 | 0.960 | 0.011 | 1.1 |
| SC3 | 2 | 0.590 | 0.638 | 0.614 | 0.024 | 3.9 | 0.673 | 0.697 | 0.685 | 0.012 | 1.8 |
| SC4 | 4 | 0.314 | 0.346 | 0.330 | 0.016 | 4.8 | 0.328 | 0.332 | 0.330 | 0.002 | 0.6 |
| SC5 | 16 | 0.060 | 0.082 | 0.071 | 0.011 | 15.5 | 0.031 | 0.031 | 0.031 | 0.000 | 0.0 |
| CS4 | | 0.093 | 0.093 | 0.093 | 0.000 | 0.0 | 0.065 | 0.064 | 0.065 | 0.001 | 0.8 |
| CS6 | | 1.225 | 0.928 | 1.077 | 0.149 | 13.8 | 0.702 | 0.678 | 0.690 | 0.012 | 1.7 |
| CS9 | | 1.661 | 1.576 | 1.619 | 0.043 | 2.6 | 1.601 | 1.573 | 1.587 | 0.014 | 0.9 |
| CS10 | | 1.267 | 1.291 | 1.279 | 0.012 | 0.9 | 1.390 | 1.420 | 1.405 | 0.015 | 1.1 |
| CS19 | | 0.367 | 0.573 | 0.470 | 0.103 | 21.9 | 0.284 | 0.325 | 0.305 | 0.021 | 6.7 |
| CS23 | | 0.016 | 0.017 | 0.017 | 0.001 | 3.0 | 0.015 | 0.015 | 0.015 | 0.000 | 0.0 |
| CS28 | | 1.373 | 1.491 | 1.432 | 0.059 | 4.1 | 1.500 | 1.550 | 1.525 | 0.025 | 1.6 |
| CS29 | | 0.016 | 0.020 | 0.018 | 0.002 | 11.1 | 0.015 | 0.015 | 0.015 | 0.000 | 0.0 |
| CS30 | | 0.839 | 0.931 | 0.885 | 0.046 | 5.2 | 0.904 | 0.918 | 0.911 | 0.007 | 0.8 |
| CS31 | | 0.650 | 0.689 | 0.670 | 0.020 | 2.9 | 0.507 | 0.574 | 0.541 | 0.034 | 6.2 |
| CS34 | | 1.284 | 1.311 | 1.298 | 0.014 | 1.0 | 1.344 | 1.300 | 1.322 | 0.022 | 1.7 |
| CS40 | | 0.836 | 0.885 | 0.861 | 0.025 | 2.8 | 0.750 | 0.743 | 0.747 | 0.004 | 0.5 |
| CS44 | | 0.228 | 0.244 | 0.236 | 0.008 | 3.4 | 0.016 | 0.015 | 0.016 | 0.001 | 3.2 |
| CS55 | | 0.880 | 0.862 | 0.871 | 0.009 | 1.0 | 0.882 | 0.846 | 0.864 | 0.018 | 2.1 |
| PBB1 | | 1.485 | 1.611 | 1.548 | 0.063 | 4.1 | 1.647 | 1.704 | 1.676 | 0.029 | 1.7 |
| PBB2 | | 1.478 | 1.633 | 1.556 | 0.078 | 5.0 | 1.458 | 1.550 | 1.504 | 0.046 | 3.1 |
| PBB3 | | 1.457 | 1.544 | 1.501 | 0.044 | 2.9 | 1.357 | 1.354 | 1.356 | 0.001 | 0.1 |

TABLE 2B-continued

| | | One-plate (bBSA coated) No transfer method | | | | | Two plate (Sav coated) Transfer step method | | | | |
|---|---|---|---|---|---|---|---|---|---|---|---|
| Sample | Rel GADab | A450 | A450 | Ave A450 | AvDev | % CV | A450 | A450 | Ave A450 | AvDev | % CV |
| PBB4 | | 1.445 | 1.503 | 1.474 | 0.029 | 2.0 | 1.585 | 1.562 | 1.574 | 0.012 | 0.7 |
| KH | | 1.143 | 1.374 | 1.259 | 0.116 | 9.2 | 1.452 | 1.398 | 1.425 | 0.027 | 1.9 |

SC = Serum calibrators
CS = patient sera
PBB = Peningula Blood Bank, control sera
KH = A control serum Determination of the Optimum Concentration of Sav Sav with four biotin binding sites acts as a bridge to bring together in a stable manner free bGAD and surface immobilized bBSA. It is, therefore, important to determine desired concentration of Sav to be added in the assay as too high or too low concentrations could adversely affect the signal for obvious reasons. A control serum pool (GADab negative) was incubated first with bGAD and then with PAD. Sav was added at different concentrations and permitted to react for 1 h at RT while shaking. The plate was washed, GAD Mab-Peroxidase conjugate bound, and the color was developed as per standard DELISA protocol. Results in Table 3 show that the signal due to bGAD binding is dependent on the presence of Sav, and the optimum range for the assay is 0.08–0.2 pmols/well.

TABLE 3

Determination of optimum Sav conc. for 'One Plate DELISA'. One plate DELISA on Nunc-bBSA plate. Unwashed stored at 4° C. A negative pool serum was used with bGAD, PAD, and conjugate. DELISA protocol was followed except that Sav was added at indicated conc. in 25 µL

| Sav pmol/well | A450 | A450 | AveA450 | AvDev | % CV |
|---|---|---|---|---|---|
| | | Expt. #1 | | | |
| 0 | 0.060 | 0.061 | 0.061 | 0.001 | 0.8 |
| 0.005 | 0.062 | 0.071 | 0.067 | 0.005 | 6.8 |
| 0.01 | 0.128 | 0.124 | 0.126 | 0.002 | 1.6 |
| 0.02 | 0.389 | 0.303 | 0.346 | 0.043 | 12.4 |
| 0.04 | 1.007 | 1.034 | 1.021 | 0.014 | 1.3 |
| 0.08 | 1.423 | 1.431 | 1.427 | 0.004 | 0.3 |
| 0.12 | 1.427 | 1.525 | 1.476 | 0.049 | 3.3 |
| 0.16 | 1.435 | 1.561 | 1.498 | 0.063 | 4.2 |
| 0.2 | 1.011 | 1.169 | 1.090 | 0.079 | 7.2 |
| 0.3 | 0.729 | 0.837 | 0.783 | 0.054 | 6.9 |
| 0.4 | 0.548 | 0.665 | 0.607 | 0.059 | 9.6 |
| 0.5 | 0.517 | 0.633 | 0.575 | 0.058 | 10.1 |
| 0.6 | 0.489 | 0.542 | 0.516 | 0.027 | 5.1 |
| 0.8 | 0.290 | 0.426 | 0.358 | 0.068 | 19.0 |

TABLE 3-continued

Determination of optimum Sav conc. for 'One Plate DELISA'. One plate DELISA on Nunc-bBSA plate. Unwashed stored at 4° C. A negative pool serum was used with bGAD, PAD, and conjugate. DELISA protocol was followed except that Sav was added at indicated conc. in 25 µL

| Sav pmol/well | A450 | A450 | AveA450 | AvDev | % CV |
|---|---|---|---|---|---|
| 1 | 0.289 | 0.371 | 0.330 | 0.041 | 12.4 |
| 2 | 0.224 | 0.287 | 0.256 | 0.032 | 12.3 |
| | | Expt. #2 | | | |
| 0 | 0.055 | 0.044 | 0.050 | 0.006 | 11.1 |
| 0.025 | 0.426 | 0.438 | 0.432 | 0.006 | 1.4 |
| 0.05 | 1.113 | 1.092 | 1.103 | 0.011 | 1.0 |
| 0.1 | 1.592 | 1.561 | 1.577 | 0.016 | 1.0 |
| 0.125 | 1.527 | 1.654 | 1.591 | 0.064 | 4.0 |
| 0.15 | 1.601 | 1.574 | 1.588 | 0.014 | 0.9 |
| 0.175 | 1.596 | 1.489 | 1.543 | 0.054 | 3.5 |
| 0.2 | 1.592 | 1.458 | 1.525 | 0.067 | 4.4 |
| 0.225 | 1.356 | 1.294 | 1.325 | 0.031 | 2.3 |
| 0.25 | 1.241 | 1.259 | 1.250 | 0.009 | 0.7 |
| 0.275 | 1.223 | 1.187 | 1.205 | 0.018 | 1.5 |
| 0.3 | 1.177 | 1.177 | 1.108 | 0.069 | 6.2 |
| 0.35 | 1.027 | 0.938 | 0.983 | 0.045 | 4.5 |
| 0.4 | 0.912 | 0.885 | 0.899 | 0.014 | 1.5 |
| 0.5 | 0.753 | 0.681 | 0.717 | 0.036 | 5.0 |

Comparison of Optimized "One Plate" Format with the "Two Plate" DELISA Using Serum Calibrators and Patient Sera Optimized single plate protocol was chosen. Briefly, serum and bGAD are reacted for 1.75 h; PAD for 0.25 h; Sav for 0.75 h; conjugate for 0.25 h and substrates for 0.5 h. The "Two Plate" (standard) DELISA protocol was used for comparison. The studies were repeated 3 times (Table 4, A, B, and C).

TABLE 4A

Comparison of results with one plate (No transfer) & two plates (with transfer) methods.
DELISA with serum calibrators, control and diabetic sera

| | One plate (bBSA coated) | | | | Two plate (Sav coated) | | | |
|---|---|---|---|---|---|---|---|---|
| Sample | A450 | A450 | AveA450 | Normalized SC1 as 100% | A450 | A450 | AveA450 | Normalized SC1 as 100% |
| SC1 | 0.888 | 0.972 | 0.930 | 100.00 | 1.301 | 1.348 | 1.325 | 100.00 |
| SC2 | 0.592 | 0.601 | 0.597 | 64.14 | 0.970 | 0.989 | 0.980 | 73.92 |
| SC3 | 0.445 | 0.437 | 0.441 | 47.42 | 0.680 | 0.708 | 0.694 | 52.38 |

TABLE 4A-continued

Comparison of results with one plate (No transfer)
& two plates (with transfer) methods.
DELISA with serum calibrators, control and diabetic sera

| Sample | One plate (bBSA coated) | | | | Two plate (Sav coated) | | | |
|---|---|---|---|---|---|---|---|---|
| | A450 | A450 | AveA450 | Normalized SC1 as 100% | A450 | A450 | AveA450 | Normalized SC1 as 100% |
| SC4 | 0.237 | 0.268 | 0.253 | 27.15 | 0.322 | 0.382 | 0.352 | 26.57 |
| SC5 | 0.055 | 0.050 | 0.053 | 5.65 | 0.042 | 0.043 | 0.043 | 3.21 |
| CW-HM1 | 0.192 | 0.161 | 0.177 | 18.98 | 0.266 | 0.319 | 0.293 | 22.08 |
| CW-HM2 | 0.709 | 0.614 | 0.662 | 71.13 | 1.146 | 1.233 | 1.190 | 89.77 |
| CW-HM3 | 0.025 | 0.105 | 0.065 | 6.99 | 0.015 | 0.016 | 0.016 | 1.17 |
| CW-HM4 | 0.843 | 0.853 | 0.848 | 91.18 | 1.641 | 1.634 | 1.638 | 123.58 |
| CW-HM5 | 0.396 | 0.395 | 0.396 | 42.53 | 0.811 | 0.763 | 0.787 | 59.40 |
| CW-HM6 | 0.694 | 0.709 | 0.702 | 75.43 | 0.651 | 0.629 | 0.640 | 48.30 |
| CW-HM7 | 0.242 | 0.246 | 0.244 | 26.24 | 0.463 | 0.480 | 0.472 | 35.58 |
| CW-HM8 | 0.529 | 0.710 | 0.620 | 66.61 | 1.366 | 1.544 | 1.455 | 109.81 |
| CW-HM9 | 0.268 | 0.306 | 0.287 | 30.86 | 0.660 | 0.764 | 0.712 | 53.74 |
| CW-HM10 | 0.643 | 0.644 | 0.644 | 69.19 | 1.488 | 1.531 | 1.510 | 113.92 |
| CW-HM11 | 0.254 | 0.265 | 0.260 | 27.90 | 0.406 | 0.422 | 0.414 | 31.25 |
| PBB1 | 1.147 | 1.147 | 1.147 | 123.33 | 1.826 | 1.769 | 1.798 | 135.66 |
| PBB2 | 0.851 | 0.898 | 0.875 | 94.03 | 1.526 | 1.582 | 1.554 | 117.28 |
| PBB3 | 0.985 | 1.060 | 1.023 | 109.95 | 1.400 | 1.432 | 1.416 | 106.87 |
| PBB4 | 0.801 | 0.909 | 0.855 | 91.94 | 1.610 | 1.721 | 1.666 | 125.70 |
| PBB6 | 0.870 | 0.888 | 0.879 | 94.52 | 1.716 | 1.668 | 1.692 | 127.70 |
| PBB7 | 1.052 | 0.932 | 0.992 | 106.67 | 1.575 | 1.646 | 1.611 | 121.55 |
| PBB8 | 0.796 | 0.999 | 0.898 | 96.51 | 1.758 | 1.779 | 1.769 | 133.47 |
| PBB9 | 0.829 | 0.773 | 0.801 | 86.13 | 1.466 | 1.563 | 1.515 | 114.30 |

CW = Patient sera
PBB = Sera from Peninsula blood bank
SC = Serum calibrator

TABLE 4B

Comparison of results with one plate (No transfer)
& two plates (with transfer) methods.
DELISA with serum calibrators, control and diabetic sera

| Sample | Expt. #2 One plate (bBSA coated) | | | | Two plate (Sav coated) | | | |
|---|---|---|---|---|---|---|---|---|
| | A450 | A450 | AveA450 | Normalized SC1 as 100% | A450 | A450 | AveA450 | Normalized SC1 as 100% |
| SC1 | 1.054 | 1.052 | 1.053 | 100.0 | 1.406 | 1.285 | 1.346 | 100.0 |
| SC2 | 0.696 | 0.701 | 0.699 | 66.3 | 1.038 | 0.878 | 0.958 | 71.2 |
| SC3 | 0.563 | 0.533 | 0.548 | 52.0 | 0.680 | 0.659 | 0.670 | 49.7 |
| SC4 | 0.294 | 0.289 | 0.292 | 27.7 | 0.365 | 0.357 | 0.361 | 26.8 |
| SC5 | 0.054 | 0.049 | 0.052 | 4.9 | 0.037 | 0.007 | 0.022 | 1.6 |
| CW-HM1 | 0.184 | 0.192 | 0.188 | 17.9 | 0.301 | 0.287 | 0.294 | 21.8 |
| CW-HM2 | 0.807 | 0.751 | 0.779 | 74.0 | 1.279 | 1.267 | 1.273 | 94.6 |
| CW-HM3 | 0.024 | 0.018 | 0.021 | 2.0 | 0.046 | 0.018 | 0.032 | 2.4 |
| CW-HM4 | 1.028 | 1.076 | 1.052 | 99.9 | 1.489 | 1.545 | 1.517 | 112.7 |
| CW-HM5 | 0.418 | 0.487 | 0.453 | 43.0 | 0.714 | 0.720 | 0.717 | 53.3 |
| CW-HM6 | 0.701 | 0.733 | 0.717 | 68.1 | 0.554 | 0.568 | 0.561 | 41.7 |
| CW-HM7 | 0.268 | 0.279 | 0.274 | 26.0 | 0.459 | 0.478 | 0.469 | 34.8 |
| CW-HM8 | 0.756 | 0.826 | 0.791 | 75.1 | 1.221 | 1.220 | 1.221 | 90.7 |
| CW-HM9 | 0.364 | 0.371 | 0.368 | 34.9 | 0.694 | 0.693 | 0.694 | 51.5 |
| CW-HM10 | 0.730 | 0.778 | 0.754 | 71.6 | 1.444 | 1.500 | 1.472 | 109.4 |
| CW-HM11 | 0.283 | 0.306 | 0.295 | 28.0 | 0.430 | 0.444 | 0.437 | 32.5 |

CW = Patient sera

TABLE 4C

Comparison of results with one plate (No transfer)
& two plates (with transfer) methods.
DELISA with serum calibrators, control and diabetic sera

| | Expt. #3 One plate (bBSA coated) | | | | Two plate (Sav coated) | | | |
|---|---|---|---|---|---|---|---|---|
| Sample | A450 | A450 | AveA450 | Normalized SC1 as 100% | A450 | A450 | AveA450 | Normalized SC1 as 100% |
| SC1 | 0.952 | 0.893 | 0.923 | 100.0 | 1.411 | 1.571 | 1.491 | 100.0 |
| SC2 | 0.677 | 0.684 | 0.681 | 73.8 | 1.012 | 1.020 | 1.016 | 68.1 |
| SC3 | 0.540 | 0.488 | 0.514 | 55.7 | 0.764 | 0.737 | 0.751 | 50.3 |
| SC4 | 0.305 | 0.277 | 0.291 | 31.5 | 0.378 | 0.408 | 0.393 | 26.4 |
| SC5 | 0.062 | 0.059 | 0.061 | 6.6 | 0.053 | 0.049 | 0.051 | 3.4 |
| CW-HM1 | 0.216 | 0.228 | 0.222 | 24.1 | 0.328 | 0.385 | 0.357 | 23.9 |
| CW-HM2 | 0.901 | 0.852 | 0.877 | 95.0 | 1.378 | 1.433 | 1.406 | 94.3 |
| CW-HM3 | 0.057 | 0.044 | 0.051 | 5.5 | 0.129 | 0.022 | 0.076 | 5.1 |
| CW-HM4 | 0.867 | 0.890 | 0.879 | 95.2 | 1.635 | 1.926 | 1.781 | 119.4 |
| CW-HM5 | 0.499 | 0.533 | 0.516 | 55.9 | 0.881 | 0.872 | 0.877 | 58.8 |
| CW-HM6 | 0.644 | 0.748 | 0.696 | 75.4 | 0.529 | 0.661 | 0.595 | 39.9 |
| CW-HM7 | 0.304 | 0.352 | 0.328 | 35.6 | 0.534 | 0.552 | 0.543 | 36.4 |
| CW-HM8 | 0.756 | 0.845 | 0.801 | 86.8 | 1.409 | 1.368 | 1.389 | 93.1 |
| CW-HM9 | 0.415 | 0.427 | 0.421 | 45.6 | 0.959 | 0.895 | 0.927 | 62.2 |
| CW-HM10 | 0.946 | 0.859 | 0.903 | 97.8 | 1.728 | 1.747 | 1.738 | 116.5 |
| CW-HM11 | 0.394 | 0.423 | 0.409 | 44.3 | 0.532 | 0.560 | 0.546 | 36.6 |

CW = Patient

The following correlations were calculated from the results:

| Expt. # | Cr | Slope | Intercept |
|---|---|---|---|
| I. Correlation between results from "One Plate" and "Two Plate DELISA. | | | |
| 1 | 0.93 | 1.67 | −0.067 |
| 2 | 0.93 | 1.40 | 0.023 |
| 3 | 0.94 | 1.75 | 0.045 |
| II. Correlation between "One Plate" DELISA repeated 3 times. | | | |
| 1 vs 2 | 0.99 | 0.83 | 0.018 |
| 1 vs 3 | 0.96 | 0.88 | −0.022 |
| 2 vs 3 | 0.97 | 1.065 | −0.049 |
| III. Correlation between "Two Plate" DELISA repeated 3 times. | | | |
| 1 vs 2 | 0.99 | 1.04 | −0.004 |
| 1 vs 3 | 0.99 | 0.92 | −0.020 |
| 2 vs 3 | 0.99 | 0.88 | −0.014 |

A good correlation (0.93) was obtained between the two methods in all 3 experiments. The reproducibility of each method was also good.

Example 2
A Competitive Assay for the Determination of Digoxin in Serum Samples

Microtiter wells are coated with biotin-BSA conjugate as described above in the Anti GAD autoantibody assay example. Anti digoxin monoclonal antibody-HRP conjugate is prepared according to Dafforn, A., et al., *Clinical Chemistry*, Vol. 36, pp. 1312–1316, 1990. Biotin-digoxin conjugate is prepared according to U.S. Pat. No. 5,340,716.

Assay Procedure

Serum sample for the determination of digoxin is diluted as required in buffer commonly used for EIA (enzyme immunoassay). The sample is added to the microtiter well and mixed with anti digoxin monoclonal antibody-HRP. The mixture is incubated with shaking for a required period. A solution containing biotin-digoxin conjugate is added to the mixture, and the reaction mixture is further incubated with shaking. At the end of this incubation period, a solution containing streptavidin is added and the mixture is further incubated with shaking. The amount of streptavidin added is dependent on the total biotin in the reaction mixture, both the biotin-digoxin conjugate and the surface bound biotin, as discribed above.

The reaction mixture is then removed from the microtiter well and the well is washed with a buffer solution commonly used in microtiter plate EIA. A solution of HRP substrate, TMB, is then added to the washed well, and enzyme reaction proceeds for the required period. The reaction is stopped by the addition of acid (as in previous example), and color development is determined using a microtiter plate reader (as in a previous example).

The extent of color development is inversely proportional to the amount of digoxin in the sample. Quantification of digoxin in the sample is carried out by comparing color development in the sample to that produced by known standard, i.e., using a standard curve produced by determination of known standards of digoxin spiked in normal serum.

Example 3
Two-site (Sandwich) Immunoassay for the Determination of Bone Specific Alkaline Phosphatase in Serum:

Anti human bone specific alkaline phosphatase, BALP, monoclonal antibodies A and B were prepared as previously described in Kurn, N., et al., *J. Bone & Mineral Research*, Vol. 9, Sup 1, p. S403. Monoclonal A and B recognize two non related epitopes of BALP, as previously demonstrated. HRP-anti BALP monoclonal antibody A conjugate is prepared according to Dafforn, A., et al., *Clinical Chemistry*, Vol. 36, pp. 1312–1316, 1990. Biotin-anti BALP monoclonal B is prepared according to Ullman, E. F., et al., *PNAS* Vol. 91 pp. 5426–5430, 1994. Microtiter wells are coated with biotin-BSA conjugate as described in the Anti GAD autoantibody assay.

Assay Procedure

An aliquot of serum sample is added to the microtiter well. A solution containing HRP-monoclonal A conjugate and biotin-monoclonal B conjugate is added to the sample and the mixture is incubated with shaking for the required period.

At the end of the first incubation period, a solution containing streptavidin is added to the well, and the mixture is further incubated with shaking. The amount of streptavidin added is dependent of the total biotin content in the reaction, including the biotin labeled monoclonal B and the surface immobilized biotin, as described before.

The reaction mixture is removed and the well is washed using a buffer solution commonly used in microtiter based EIA.

A solution of HRP substrate, TMB, is added to the well. Enzyme reaction is allowed to proceed for the required period, and the enzyme reaction is stopped by addition of acid, as described in previous example.

Color development is determined using a microtiter plate reader as in previous example.

The extent of enzyme activity is directly proportional to the amount of BALP in the sample. A series of standards composed of known amounts of BALP spiked into serum, are used for construction of a standard curve for the quantification of BALP in the sample.

All references cited herein are incorporated by reference.

The invention has been described in detail with particular reference to the preferred embodiments thereof. However, it will be appreciated that modifications and improvements within the spirit and teachings of the inventions may be made by those in the art upon considering the present disclosure.

We claim:

1. A method of determining the presence or amount of a specific antibody to an antigen, in a sample suspected of containing the antibody, the method comprising the steps of:
   a) forming a mixture comprising:
      (i) the sample;
      (ii) the antigen coupled to a first binding agent, wherein the antibody, if present, binds the antigen to form a first binding agent/antigen/antibody complex;
      (iii) a support comprising a second binding agent;
   b) adding to the mixture a masking compound that binds the complex and does not bind the antigen coupled to the first binding agent when the antigen coupled to the first binding agent is not part of the complex;
   c) adding to the mixture an activator molecule which binds both of (1) the first binding agent coupled to the antigen when the first binding agent coupled to the antigen is not part of the complex, and (2) the second binding agent of the support, and
   d) determining the amount of the antibody in the sample by detecting the presence or amount of antigen immobilized on the support, wherein the presence or amount of immobilized antigen is related to the presence or amount of the antibody in the sample.

2. The method according to claim 1, wherein the first binding agent and the second binding agent are the same.

3. The method of claim 1 wherein the activator is a multivalent molecule.

4. The method according to claim 3, wherein the multivalent molecule is selected from the group consisting of avidin, streptavidin, anti-biotin IgG, antibiotin IgM, lectin, a multimeric synthetic peptide, and folate dextran conjugate.

5. The method according to claim 1, wherein the first binding agent and the second binding agent are different and the activator is a heterofunctional molecule having a first binding site that binds the first binding agent and a second binding site that binds the second binding agent.

6. The method according to claim 1, wherein the first and second binding agents are each selected from biotin, fluorescein, folic acid binding protein, haptens, carbohydrates or receptors.

7. The method according to claim 1, wherein the first and second binding agents comprise biotin and the activator comprises avidin, streptavidin or anti-biotin antibody.

8. The method according to claim 7, wherein the number of binding sites on avidin or streptavidin added is less than or equal to the total equivalents of biotin bound to the support and the antigen.

9. The method according to claim 8, wherein the number of binding sites on avidin or streptavidin is one-half the total equivalents biotin comprising the first and second binding agents.

10. The method according to claim 1, wherein the first binding agent is a receptor and the activator is a ligand for the receptor.

11. The method according to claim 10, wherein the first binding agent comprises folate binding protein and the bivalent or multivalent molecule comprises a folate-dextran conjugate.

12. The method according to claim 1, wherein the support is selected from the surface of a container, beads, glass, polystyrene, polypropylene, polyethylene, dextran, nylon, amylases, natural and modified celluloses, polyacrylamides, agarose and magnetite.

13. The method according to claim 1, wherein the determining step comprises providing one or more signal producing system members and measuring the signal produced by the signal producing system members, the presence or amount thereof being related to the presence or amount of the antibody in the sample.

14. The method according to claim 13 wherein at least one of the signal producing system members is selected from the group consisting of fluorescers, enzymes, chemiluminescers, photosensitizers and suspendable particles.

15. The method according to claim 14, wherein the determining step involves the detection of enzyme activity, luminescence or light absorbance.

16. The method according to claim 14, wherein the antigen is bound to one of the signal producing system members.

17. The method according to claim 1, further comprising between steps (c) and (d) the step of adding of a signal producing system member bound to a specific binder to the antigen and step (d) further comprises detecting the signal.

18. The method according to claim 17, wherein the specific binder is directly or indirectly bound to a label.

19. The method according to claim 1, wherein the masking compound is selected from the group consisting of antibodies to immunoglobulins, complement factor C1q, rheumatoid factor, protein G and protein A.

20. The method according to claim 19, wherein the masking compound is bound to a suspendable solid phase or soluble polymer.

21. The method according to claim 20, wherein the suspendable solid phase is a particle comprised of a material selected from the group consisting of polymers, ceramic and glass.

22. The method according to claim 20, wherein the soluble polymer has a molecular weight of over 250,000.

23. The method according to claim 1, wherein the determining step further comprises separating the support from the mixture and contacting the support with a specific binder for the antigen.

24. The method according to claim 1, wherein the antibody is an autoantibody to glutamic acid decarboxylase or insulin.

25. A method of determining the presence or amount of a specific antibody to an antigen in a sample suspected of containing the antibody, comprising the steps of:
   a) forming a mixture comprising coupled antigen-antibody complexes by admixing, in contact with a support, the sample with a coupled antigen, wherein the coupled antigen is the antigen coupled to a first binding agent, wherein the coupled antigen-antibody complex is formed only if the sample contains an antibody specific for the antigen, and wherein the support comprises a second binding agent;
   b) adding a masking compound to the mixture in contact with the support, wherein the masking compound binds to the coupled antigen-antibody complex, but does not substantially bind to the coupled antigen alone, to form a mixture comprising masked coupled antigen-antibody complexes in contact with the support;
   c) adding an activator molecule to the mixture in contact with the support, wherein the activator molecule binds both un-masked coupled antigen and the second binding agent of the support, thereby immobilizing the un-masked coupled antigen to the support;
   d) detecting the presence or amount of the unmasked coupled antigen immobilized to the support, wherein the presence of amount of the unmasked immobilized coupled antigen is related to the presence or amount of the specific antibody in the sample, thereby determining the presence or amount of a specific antibody to the antigen in the sample.

26. The method of claim 25 wherein the coupled antigen is not substantially immobilized to the support in the absence of the activator molecule.

27. The method according to claim 25, wherein the first binding agent and the second binding agent are the same.

28. The method according to claim 27, wherein the multivalent molecule is selected from the group consisting of avidin, streptavidin, anti-biotin IgG, antibiotin IgM, lectin, a multimeric synthetic peptide, and folate dextran conjugate.

29. The method of claim 25 wherein the activator is a multivalent molecule.

30. The method according to claim 25, wherein the first binding agent and the second binding agent are different and the activator is a heterofunctional molecule having a first binding site that binds the first binding agent and a second binding site that binds the second binding agent.

31. The method according to claim 25, wherein the first and second binding agents are each selected from the group consisting of biotin, fluorescein, folic acid binding protein, haptens, carbohydrates and receptors.

32. The method according to claim 25, wherein the first and second binding agents comprise biotin and the activator comprises avidin, streptavidin or anti-biotin antibody.

* * * * *